United States Patent
Juto et al.

(10) Patent No.: US 9,579,247 B2
(45) Date of Patent: Feb. 28, 2017

(54) TREATMENT OF HEADACHE DISORDERS

(71) Applicant: CHORDATE MEDICAL AB, Kista (SE)

(72) Inventors: Jan-Erik Juto, Stockholm (SE); William Holm, Stockholm (SE); Fredrik Juto, Stockholm (SE)

(73) Assignee: CHORDATE MEDICAL AB, Kista (SE)

( * ) Notice: Subject to any disclaimer, the term of this patent is extended or adjusted under 35 U.S.C. 154(b) by 593 days.

(21) Appl. No.: 13/714,643

(22) Filed: Dec. 14, 2012

(65) Prior Publication Data

US 2013/0158450 A1 Jun. 20, 2013

Related U.S. Application Data

(60) Provisional application No. 61/576,756, filed on Dec. 16, 2011.

(30) Foreign Application Priority Data

Dec. 16, 2011 (EP) .................... 11194085

(51) Int. Cl.
*A61H 23/04* (2006.01)
*A61H 21/00* (2006.01)
(Continued)

(52) U.S. Cl.
CPC .............. *A61H 1/00* (2013.01); *A61H 9/0078* (2013.01); *A61H 21/00* (2013.01); *A61H 23/02* (2013.01);
(Continued)

(58) Field of Classification Search
CPC ...... A61H 9/0078; A61H 23/04; A61H 21/00; A61H 2230/505; A61H 2230/045;
(Continued)

(56) References Cited

U.S. PATENT DOCUMENTS 901,376 A 10/1908 Roberts
912,205 A 2/1909 Talcott
(Continued)

FOREIGN PATENT DOCUMENTS

CH 329193 A 4/1958
EP 0935980 A1 8/1999
(Continued)

OTHER PUBLICATIONS

Papon et al., "Nasal wall compliance in vasomotor rhinitis," J. Appl. Physiol., vol. 100, 2006 (First published Sep. 1, 2005), pp. 107-111, XP055055268.
(Continued)

*Primary Examiner* — Justine Yu
*Assistant Examiner* — Douglas Sul
(74) *Attorney, Agent, or Firm* — Birch, Stewart, Kolasch & Birch, LLP

(57) ABSTRACT

A method for treatment of a headache disorder in a human subject is provided. The method includes a) selecting a treatment area in the nasal cavity of the human subject; b) providing a stimulation member arranged for vibration stimulation of the selected treatment area; c) introducing the stimulation member into a nasal cavity of the human subject; d) expanding the stimulation member to exert a pressure on tissue of the selected treatment area; and e) bringing the stimulation member to vibrate in the nasal cavity to impart vibrations to the selected treatment area.

23 Claims, 11 Drawing Sheets

(51) Int. Cl.
*A61H 1/00* (2006.01)
*A61H 9/00* (2006.01)
*A61H 23/02* (2006.01)
*G06F 19/00* (2011.01)

(52) U.S. Cl.
CPC ......... *A61H 23/04* (2013.01); *G06F 19/3481* (2013.01); *A61H 2201/0103* (2013.01); *A61H 2201/5071* (2013.01); *A61H 2205/023* (2013.01); *A61H 2230/045* (2013.01); *A61H 2230/065* (2013.01); *A61H 2230/105* (2013.01); *A61H 2230/505* (2013.01)

(58) Field of Classification Search
CPC ........ A61H 2230/065; A61H 2230/101; A61H 2201/123; A61H 2201/5071; A61N 1/0529; A61N 1/0534; A61N 2001/36039; A61N 1/36071; A61N 2001/36075
See application file for complete search history.

(56) References Cited

U.S. PATENT DOCUMENTS

| | | | |
|---|---|---|---|
| 961,034 | A | 6/1910 | Siebert et al. |
| 1,735,519 | A | 11/1929 | Vance |
| 1,764,838 | A | 6/1930 | Horne |
| 2,052,321 | A * | 8/1936 | Smart ................. 604/94.01 |
| 2,101,273 | A | 12/1937 | Smith |
| 3,612,211 | A | 10/1971 | Clark, III |
| 3,848,607 | A | 11/1974 | St. Clair |
| 4,462,411 | A | 7/1984 | Rickards |
| 4,911,149 | A | 3/1990 | Borodulin et al. |
| 5,139,510 | A | 8/1992 | Goldsmith, III et al. |
| 5,609,606 | A | 3/1997 | O'Boyle |
| 5,682,881 | A | 11/1997 | Winthrop et al. |
| 5,903,516 | A | 5/1999 | Greenleaf et al. |
| 6,159,170 | A | 12/2000 | Borodulin et al. |
| 6,193,680 | B1 | 2/2001 | Parsons et al. |
| 6,230,049 | B1 * | 5/2001 | Fischell ............... A61B 5/0476 600/544 |
| 6,358,272 | B1 | 3/2002 | Wilden |
| 6,709,406 | B2 * | 3/2004 | Laserow ............... 600/552 |
| 8,317,816 | B2 | 11/2012 | Becker |
| 2001/0051819 | A1 | 12/2001 | Fischell et al. |
| 2002/0072781 | A1 | 6/2002 | Lattner et al. |
| 2002/0177889 | A1 | 11/2002 | Brisken et al. |
| 2003/0087734 | A1 | 5/2003 | Kring et al. |
| 2003/0195578 | A1 * | 10/2003 | Perron et al. .............. 607/27 |
| 2004/0096089 | A1 * | 5/2004 | Borsook et al. .......... 382/131 |
| 2004/0097850 | A1 | 5/2004 | Plante |
| 2004/0138536 | A1 * | 7/2004 | Frei et al. ................ 600/300 |
| 2004/0172112 | A1 | 9/2004 | Cioanta et al. |
| 2004/0220644 | A1 * | 11/2004 | Shalev et al. .............. 607/45 |
| 2004/0230252 | A1 | 11/2004 | Kullok et al. |
| 2004/0243172 | A1 | 12/2004 | Hogle |
| 2005/0011518 | A1 | 1/2005 | Biondo et al. |
| 2005/0021092 | A1 | 1/2005 | Yun et al. |
| 2005/0054958 | A1 | 3/2005 | Hoffmann |
| 2006/0094992 | A1 | 5/2006 | Imboden et al. |
| 2006/0190022 | A1 | 8/2006 | Beyar et al. |
| 2007/0149905 | A1 | 6/2007 | Hanna |
| 2008/0027487 | A1 * | 1/2008 | Patel et al. ................. 607/2 |
| 2008/0198330 | A1 | 8/2008 | Taylor |
| 2008/0200848 | A1 | 8/2008 | Avni |
| 2008/0208168 | A1 | 8/2008 | Garabet |
| 2008/0243204 | A1 * | 10/2008 | Uthman et al. ............. 607/45 |
| 2008/0281238 | A1 | 11/2008 | Oohashi et al. |
| 2009/0005713 | A1 | 1/2009 | Podrazhansky et al. |
| 2009/0118786 | A1 | 5/2009 | Meadows et al. |
| 2009/0157141 | A1 * | 6/2009 | Chiao et al. ............... 607/46 |
| 2009/0187098 | A1 | 7/2009 | Makower et al. |
| 2010/0004709 | A1 | 1/2010 | Mische |
| 2010/0094209 | A1 | 4/2010 | Drasler et al. |
| 2010/0228075 | A1 | 9/2010 | Lu |
| 2010/0234840 | A1 | 9/2010 | Jackson et al. |
| 2010/0249637 | A1 | 9/2010 | Walter et al. |
| 2010/0286576 | A1 | 11/2010 | Pryor et al. |
| 2010/0286626 | A1 * | 11/2010 | Petersen ............... A61B 1/0055 604/264 |
| 2011/0190668 | A1 | 8/2011 | Mishelevich |
| 2011/0270138 | A1 | 11/2011 | Mishelevich |

FOREIGN PATENT DOCUMENTS

| | | |
|---|---|---|
| FR | 592104 A | 7/1925 |
| FR | 838034 A | 2/1939 |
| FR | 920885 A | 4/1947 |
| GB | 385992 A | 1/1933 |
| GB | 1217760 A | 12/1970 |
| JP | 2001-17500 A | 1/2001 |
| JP | 2001-37883 A | 2/2001 |
| KR | 10-1019957 B1 | 3/2011 |
| RU | 2099039 C1 | 12/1997 |
| RU | 2199303 C1 | 2/2003 |
| SU | 1148614 A | 4/1985 |
| SU | 1560205 A1 | 4/1990 |
| WO | WO 86/01399 A1 | 3/1986 |
| WO | WO 96/36396 A2 | 11/1996 |
| WO | WO 96/39218 A1 | 12/1996 |
| WO | WO 01/41695 A2 | 6/2001 |
| WO | WO 2004/047675 A2 | 6/2004 |
| WO | WO 2004/105579 A2 | 12/2004 |
| WO | WO 2006/114783 A2 | 11/2006 |
| WO | WO 2008/138997 A1 | 11/2008 |
| WO | WO 2010/033055 A1 | 3/2010 |

OTHER PUBLICATIONS

Klinger et al., "Untersuchungen zur Mikro-zirkulation der Nasenschleimhaut bei Verwendung von Ballon-tamponaden", Laryngo-Rhino-Otol., vol. 76, 1997, pp. 127-130, XP008066107.
Alstadhaug, "Migraine and the Hypothalamus", Cephalalgia, 2009, pp. 1-9.
Ansarinia et al., "Electrical Stimulation of Sphenopalatine Ganglion for Acute Treatment of Cluster Headaches", Headache, Jul. 2010, pp. 1164-1174.
Bar-Shir et al., "Late Stimulation of the Sphenopalatine-Ganglion in Ischemic Rats: Improvement in N-Acetyl-Aspartate Levels and Diffusion Weighted Imaging Characteristics as Seen by MR", Journal of Magnetic Resonance Imaging, vol. 31, 2010, pp. 1355-1363.
Brown et al., "Towards a Physiology-Based Measure of Pain: Patterns of Human Brain Activity Distinguish Painful from Non-Painful Thermal Stimulation", Plos One, vol. 6, Iss. 9, e24124, Sep. 2011, pp. 1-8.
Kim et al., "Predicting the Timing of Spikes Evoked by Tactile Stimulation of the Hand", J Neurophysiol, vol. 104, 2010, pp. 1484-1496.
Krajnak et al., "Characterization of Frequency-Dependent Responses of the Vascular System to Repetitive Vibration", JOEM, vol. 52, No. 6, Jun. 2010, pp. 584-594.
Kuncel et al., "Selection of Stimulus Parameters for Deep Brain Stimulation", Clinical Neurophysiology, vol. 115, 2004, pp. 2431-2441.
Leroux et al., "Cluster Headache", Orphanet Journal of Rare Diseases, vol. 3, No. 20, 2008, 11 pages provided.
Ludwig, "The Velocity of Sound through Tissues and the Acoustic Impedance of Tissues", The Journal of the Acoustical Society of America, vol. 22, No. 6, Nov. 1950, 5 pages provided.
Malm, "Measurement of Nasal Patency", Allergy, vol. 52 (suppl. 40), 1997, pp. 19-23.
Malm, "Stimulation of Sympathetic Nerve Fibres to the Nose in Cats", Acta Otolaryng, vol. 75, 1973, pp. 519-526.
Salansky et al., "Responses of the Nervous System to Low Frequency Stimulation and EEG Rhythms: Clinical Implications", Neuroscience and Biobehavioral Reviews, vol. 22, No. 3, 1998, pp. 395-409.
Tepper et al., "Acute Treatment of Intractable Migraine With Sphenopalatine Ganglion Electrical Stimulation", Headache, vol. 49, Jul. 2009, pp. 983-989.

(56) References Cited

OTHER PUBLICATIONS

VBM, "VBM Tube Fixations", VBM Medizintechnik GmbH, 2006, 6 pages provided.
Zelena, "Nerves and Mechanoreceptors: The Role of Innervations in the Development and Maintenance of Mammalian Mechanoreceptors", Springer, 1994, pp. 147-148.
U.S. Appl. No. 13/714,634, filed Dec. 14, 2012.
U.S. Appl. No. 13/714,636, filed Dec. 14, 2012.
U.S. Appl. No. 13/714,726, filed Dec. 14, 2012.
U.S. Appl. No. 13/714,649, filed Dec. 14, 2012.
U.S. Appl. No. 13/714,612, filed Dec. 14, 2012.

* cited by examiner

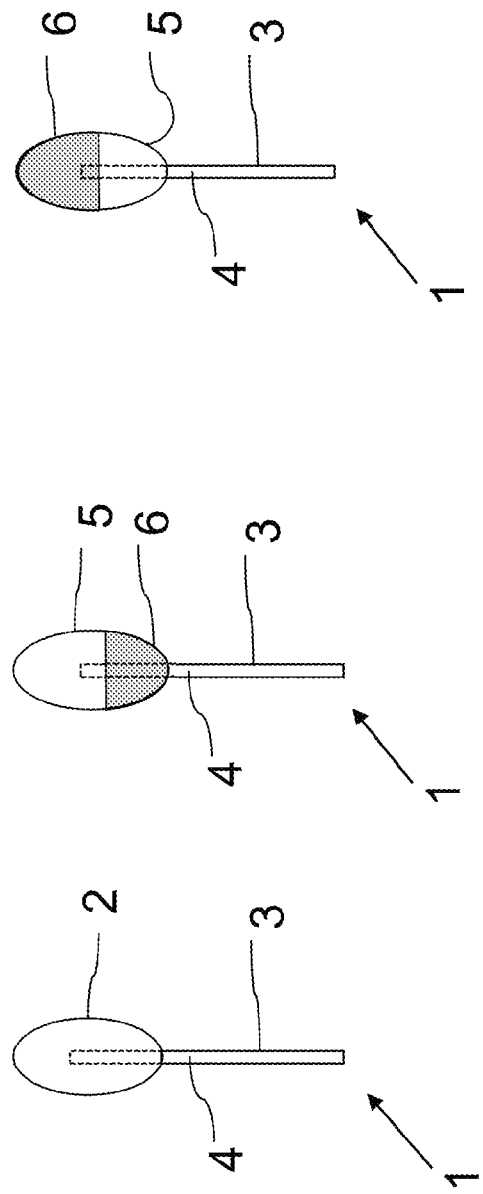
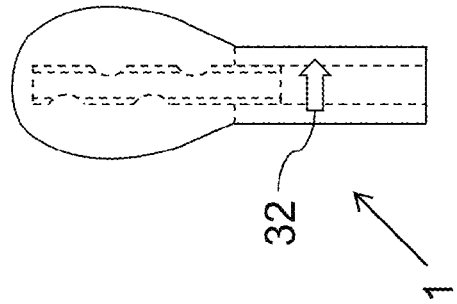
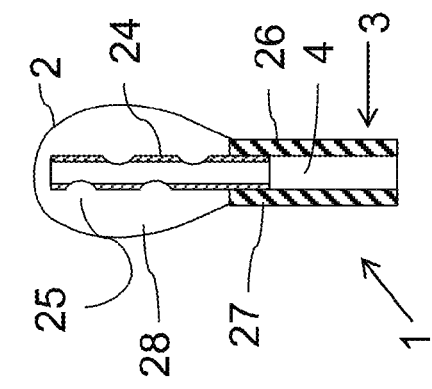

TREATMENT OF HEADACHE DISORDERS

CROSS-REFERENCE TO RELATED APPLICATIONS

This application claims priority under 35 U.S.C. §119(e) to U.S. Provisional Application No. 61/576,756 filed on Dec. 16, 2011. This application also claims priority under 35 U.S.C. §119(a) to Application No. 11194085.4, filed in Europe on Dec. 16, 2011. The entirety of each of the above-identified applications is expressly incorporated herein by reference.

BACKGROUND OF THE INVENTION

1. Field of the Invention

The present invention relates to devices and methods for treatment of a headache disorder by imparting vibrations to parts of the nasal cavity of a human subject suffering from a headache disorder.

2. Description of Background Art

Sphenopalatine ganglion is a parasympathetic ganglion found in the pterygopalatine fossa. It is one of four parasympathetic ganglia of the head and neck. It consists of the largest aggregate of neurons in the head outside of the brain. The sphenopalatine ganglion has been associated with a wide variety of pain problems that range from pain in the head and neck to pain in the low back. For example, electrical stimulation of the sphenopalatine ganglion has been shown to relieve acute severe cluster headache pain (Ansarinia et al, *Headache;* 2010, 50:1164-1174). In other examples, blocking of the sphenopalatine ganglion has been successful for reducing pain associated with headache.

The hypothalamus is a portion of the brain which lies beneath the thalamus and which contains a number of small nuclei with a variety of functions. One of the most important functions of the hypothalamus is to provide a link between the nervous system and the endocrine system via the pituitary gland (hypophysis). The hypothalamus has an influence on certain metabolic processes by secreting certain neurohormones, often called hypothalamic-releasing hormones, which in turn stimulate or inhibit the secretion of pituitary hormones. It also regulates other glands such as the ovaries, parathyroids and thyroid and has a degree of control over sleeping patterns, eating, drinking and speech. Moreover, the hypothalamus is involved in the regulation of body temperature, water balance, blood sugar and fat metabolism. Several illnesses are associated with hypothalamic dysfunction, such as migraine, Ménière's disease, hypertension, cluster headache, arrhythmia, ALS, irritable bowel syndrome, sleep disorders, diabetes, obesity, multiple sclerosis, tinnitus, Alzheimer's disease, mood and anxiety disorders and epilepsy. In many cases the connection between the hypothalamus and the illness in question is not fully understood. In addition, many of the illnesses listed above lack satisfactory therapies.

Ménière's disease (MD), for example, is a relatively rare disease affecting the inner ear. The disease is characterized by episodic vertigo, fluctuating hearing loss, aural pressure and tinnitus. MD is a progressive disorder that most often results in severe hearing deterioration. No otoprotective interventions currently exist and chemical or surgically destructive procedures are used for treatment beyond the acute phase.

Cluster headache (CH), also called Horton's headache, is another example of an illness with a suggested connection to hypothalamus and which lacks a successful treatment method. CH is the most severe disorder among primary headache disorders. It is characterized by recurrent short-lasting attacks of torturous unilateral periorbital pain, mostly accompanied by ipsilateral autonomic signs such as nasal congestion, ptosis, lacrimation and redness of the eye. Ipsilateral autonomic signs are signs of autonomic dysfunction; ipsilateral lacrimation, redness of the eye and nasal congestion are signs of parasympathetic hyperactivity, and the combination of ptosis and miosis is a sign of sympathetic hypoactivity. New surgical therapies have been tested. However, these treatments are invasive and can cause severe complications. The pathophysiology of CH is currently unknown, but involvement of the hypothalamus and the parasympathetic nervous system has been proposed (Leoux E et al, *Orphanet J of Rare Diseases;* 2008, 3:20)

Yet another example of an illness where involvement of hypothalamus has been suggested is migraine (Alstadhaug K B, *Cephalalgia;* 2009, 29: 809). Migraine is a complex multi-factorial disorder of the brain that is characterized by episodes of headache and super-sensitivity to sensory stimuli. Migraine is a type of primary headache disorder, and can be broadly categorized as migraine without aura and migraine with aura. The clinical features in migraine are thought to result from dysfunction of the parasympathetic nervous system.

There are several known devices for conducting treatments with systemic effects in patients. Devices for use in for example the nasal cavity however often aim at achieving a local effect, such as decongesting the nasal mucosa, and may often be used in combination with a chemical substance. One example of a device for achieving a local effect on the nasal mucosa is disclosed in WO 2008/138997.

Devices are also known that by mechanical vibration in a body cavity affect body functions, e.g. in the ear or over a body surface. In US 2008/281238, a system for increasing activity in the fundamental brain is disclosed. The disclosed system comprises a first and a second vibration applying device, wherein the first vibration applying device applies vibrations having frequency components within an audible range to the auditory sense system of a living body. The second vibration applying device applies vibrations having super-high frequency components exceeding the audible range to another region than the auditory sense system, such as the nasal cavity.

In RU 2199303 there is disclosed a method of treating the neuroautonomic form of vasomotor rhinitis. More specifically, the method involves vibratory massage of the anterior third of the inferior and middle concha at a frequency of 50 Hz for 1.5-2 minutes in combination with vibratory massage of certain biological active points (BAP:s) located in the hand, chin and near the nose. The instrument used for delivering the vibratory massage is described as a vibromassage instrument having a ball and a tip.

In US 2011/190668, methods and systems for non-invasive neuromodulation of the sphenopalatine ganglion is disclosed. An ultrasound transducer to treat migraine and cluster headache is described. An acoustic frequency, e.g. 0.44 MHz (typically in the range of 0.3 to 0.8 MHz), which permits the ultrasound to effectively penetrate through bone, is used.

In US 2007/149905, a device for mechanically treating headache is disclosed. Headache is treated by head massage carried out via a headpiece with vibrators in a frequency range of 50 to 350 Hz applied in bursts with a duty cycle of 10-20%.

SUMMARY OF THE INVENTION

It is an object of the present invention to provide novel methods and devices for treatment of headache disorders.

There is, in a first aspect of the invention, provided a system for treatment of a headache disorder in a human subject, comprising at least one expandable stimulation member being arrangable in a first state wherein the stimulation member can be introduced into the nasal cavity of a human subject, and in a second state wherein the stimulation member is expanded to a volume such that the stimulation member abuts against the tissue of the nasal cavity;

wherein the stimulation member comprises at least one stimulating portion that in said second state is arranged to abut against tissue of at least one of the anterior and the posterior part of the nasal cavity and to impart vibrations to said part of the nasal cavity, and at least one retaining portion that in said second state is arranged to abut against tissue of the nasal cavity;

a frequency regulating module arranged to control the frequency of the vibrations imparted by the at least one stimulating portion of the at least one stimulation member to the nasal cavity;

an amplitude regulating module arranged to control the amplitude of the vibrations imparted by the at least one stimulating portion of the at least one stimulation member to the nasal cavity, and a pressure regulating module arranged to control the pressure at which the at least one stimulating portion of the at least one stimulation member abuts against the tissue of the nasal cavity;

a control unit arranged to direct vibrations to at least one of the posterior and the anterior part of the nasal cavity by controlling operation of said regulating modules, and comprising a user interface arranged to receive input information related to said headache disorder from a user and transmit instructions regarding said treatment.

Vibratory stimulation in the nasal cavity with a system according to the first aspect may thus be beneficial for patients suffering from different headache disorders such as primary and secondary headaches. The level of pain as experienced by the human subject can be measured directly or indirectly, subjectively or objectively by different methods. The patient being subjected to the treatment may himself/herself indicate the level of pain he/she experiences, or functional neuroimaging may be used for achieving an objective measure of the pain. The treatment evidently aims at reducing or eliminating the pain experienced by the human subject.

The vibration stimulation in the nasal cavity of a human subject may affect different treatment targets in the human body. A treatment target as used herein should be understood as a target site for vibration stimulation within the human body. By stimulating different treatment targets, different headache disorders may be treated. One example of a treatment target is the sphenopalatine ganglion. Studies have shown that the sphenopalatine ganglion may be associated with a wide variety of pain problems. By stimulating the sphenopalatine ganglion with vibrations headache disorders associated with a dysfunction of the sphenopalatine ganglion can be affected and the symptoms, such as pain, can be reduced. Another example of a treatment target is the hypothalamus. By stimulating the hypothalamus with a system according to the present invention, headache disorders associated with a dysfunction of the hypothalamus can be affected and the symptoms can be reduced.

In a system according to the first aspect, at least one of the parameters vibration frequency, vibration amplitude and abutting pressure may be independently regulated. The regulating modules of the system are controlled by means of a control unit. In an alternative embodiment, they could be controlled manually.

The regulating modules are arranged to control their respective outputs. In this context, control should be understood as delivering a constant value. This can be either a fixed value being constant for all treatments, meaning that the regulating module either delivers this particular value or no output at all. An alternative is that the regulating module can accept an input adjusting the delivered output value. It is within the scope of the invention that two or three regulating modules are comprised within the same regulating module. An example could be an oscillation pump comprising a piston reciprocating within a cylinder, such a pump can be used as a frequency and amplitude regulating module. In such a case the amplitude would typically be fixed (corresponding to the stroke of the piston) and the frequency would be possible to vary (e.g. corresponding to a rotation rate of a motor driving the piston).

The user interface may comprise instructions for an operator or the human subject that enables less trained persons to efficiently and safely use the system. This can be an advantageous way to distribute the knowledge needed to cure or alleviate headache disorders. The user interface may provide step by step instructions and give the operator or the human subject an opportunity to confirm that the required instructions has been followed. The user interface may further be used to collect input information by prompting for the desired information. By only allowing a limited number of responses, e.g. by selection from fixed entries, the inclusion of a suitable user interface ensures that the system works as intended. Furthermore the user interface may show the progress of the treatment. This may be in the form of a progress bar showing the remaining treatment time.

The stimulation member of the system may, when positioned within the nasal cavity of a human subject, reach structures in an anterior and a posterior part of the nasal cavity. In some instances, vibrations may be directed such that specific structures in the nasal cavity are subjected to the vibratory stimulation via the stimulation member of the system. Vibratory stimulation in the posterior part of the nasal cavity may stimulate bone structures in the nasal cavity connected to the cranium, such as parts of the inferior, middle and/or superior conchae, e.g. posterior two thirds of the inferior and middle conchae, and thus mechanically transmit vibrations to e.g. the hypothalamus. Vibratory stimulation in the anterior part of the nasal cavity may stimulate bone structures in the nasal cavity connected to the face, such as parts of the inferior and middle conchae; e.g. the part of the nasal cavity from the nostril to the anterior third of the inferior and middle conchae, and thus mechanically transmit vibrations to e.g. the sphenopalatine ganglion. In another embodiment, the system may furthermore comprise a control module arranged to impart vibrations sequentially to the posterior and anterior part of the nasal cavity.

The stimulation member of the device may thus impart vibrations to different parts of the nasal cavity. In one example, the device comprising the stimulating member may have different configurations for stimulation of the different parts of the nasal cavity. The different configurations of a device may be specific for treatment of specific headache disorders. In particular, the different configurations may consist in different stimulating portions, being arranged to impart vibrations to specific parts of the nasal cavity, such as the anterior or the posterior part of the nasal cavity. The stimulation member also comprises at least one retaining portion arranged to retain the stimulation member at a fixed position in the nasal cavity during vibratory stimulation without necessarily imparting vibrations to surrounding tissue.

In one embodiment, the at least one retaining portion is arranged to abut against tissue in an outer part of the nostril of the human subject.

In one embodiment, the at least one stimulation member comprises at least one of an anterior stimulating portion arranged to abut against tissue of the anterior part of the nasal cavity and to impart vibrations to the anterior part of the nasal cavity, and a posterior stimulating portion arranged to abut against tissue of the posterior part of the nasal cavity and to impart vibrations to the posterior part of the nasal cavity.

In one embodiment, the at least one stimulation member comprises an anterior stimulating portion arranged to abut against the anterior part of the nasal cavity and to impart vibrations to the anterior part of the nasal cavity; an outer retaining portion arranged to abut against tissue in an outer part of the nostril of the human subject, and a posterior retaining portion arranged to abut against tissue in the posterior part of the nasal cavity.

In one embodiment, the at least one stimulation member comprises a posterior stimulating portion arranged to abut against the posterior part of the nasal cavity and to impart vibrations to the posterior part of the nasal cavity; an outer retaining portion arranged to abut against tissue in an outer part of the nostril of the human subject, and an anterior retaining portion arranged to abut against tissue in the anterior part of the nasal cavity.

In one embodiment, the at least one stimulating member comprises both an anterior stimulating portion and a posterior stimulating portion.

In one embodiment, the regulating modules are arranged to independently adjust the frequency of the vibrations imparted by the anterior and posterior stimulating portions, the amplitude of the vibrations imparted by the anterior and posterior stimulating portions, and the pressure at which the anterior and posterior stimulating portions abut against the tissue.

In another embodiment, the system comprises a plurality of devices each comprising geometrically different stimulation members. The stimulation members may for example differ in shape as well as in length, width and/or diameter. By selection and use of a stimulation member from a plurality of stimulation members, any influence differences in nasal anatomy may have on stimulation is reduced. In embodiments where the system comprises an analyzing module, such a module may moreover be arranged to compare the response received by stimulation with a specific stimulation member with an expected response range. If the response received does not correspond to the expected response, the analyzing module may prompt e.g. an operator to exchange the stimulation member accordingly. The individual devices comprised within the plurality of devices may be specific for treatment of different parts of the nasal cavity, such as the anterior and posterior part.

The plurality of devices may also comprise stimulation members having different arrangements of stimulating and retaining portions. For example the arrangements of stimulating portions and retaining portions as described above.

In one embodiment, the user interface is arranged to instruct the user on which type of stimulation member to use for headache treatment, said type being selected from a plurality of stimulation members. In this context, the type of stimulation member may be selected from any one of the above described pluralities of stimulation members. The stimulation member may for example be selected from a stimulation member comprising an anterior stimulating portion arranged to abut against the anterior part of the nasal cavity and to impart vibrations to the anterior part of the nasal cavity; an outer retaining portion arranged to abut against tissue in an outer part of the nostril of the human subject, and a posterior retaining portion arranged to abut against tissue in the posterior part of the nasal cavity; and a stimulation member comprising a posterior stimulating portion arranged to abut against the posterior part of the nasal cavity and to impart vibrations to the posterior part of the nasal cavity; an outer retaining portion arranged to abut against tissue in an outer part of the nostril of the human subject, and an anterior retaining portion arranged to abut against tissue in the anterior part of the nasal cavity.

In one embodiment, the user interface is further arranged to instruct the user where to position the stimulation member, said position being selected from the left and right nasal cavity.

In one embodiment, the user interface is further arranged to receive input information related to the type and position of the stimulation member, and wherein the control unit is arranged to receive this information from the user interface and direct vibrations accordingly. Thus, dependent on the type and position of the stimulation member, different vibration stimulation parameters may be applied.

In one embodiment the interface is arranged to receive a confirmation input from the user confirming that instructions regarding type and position of stimulation member have been followed The stimulation member, and in particular the stimulating portion, may furthermore be arranged to abut against tissue in different parts of the nasal cavity, such as the anterior and/or posterior part of the nasal cavity. This provides direct contact between the stimulation member and the tissue of the nasal cavity. Moreover, the stimulation member can be arranged to abut against the tissue of the nasal cavity at a pressure of between approximately 20 and 120 mbar.

In one embodiment, the control unit is arranged to direct vibrations to the anterior part of the nasal cavity by controlling the pressure regulating module to adjust the pressure at which the at least one stimulating portion abuts against the tissue of the anterior part of the nasal cavity to be in the range of 20 to 80 mbar. The applicant has found that by controlling the pressure of the stimulating portion, the positioning of the stimulation member may be facilitated and specific treatment sites within the nasal cavity may be reached.

In one embodiment, the control unit is arranged to direct vibrations to the posterior part of the nasal cavity by controlling the pressure regulating module to adjust the pressure at which the at least one stimulating portion abuts against the tissue of the posterior part of the nasal cavity to be in the range of 81 to 120 mbar such as in the range of 90 to 105 mbar.

In addition, the stimulation member may, in one embodiment, be arranged to impart vibrations at a frequency of between 40 and 100 Hz to the nasal cavity, such as between approximately 50 Hz and 80 Hz, such as between approximately 50 Hz and 70 Hz, such as between approximately 60 Hz and 70 Hz. The applicant has found that such low frequency vibrations applied to tissue in the nasal cavity may provide effective treatment for patients suffering from severe headache disorders.

In another embodiment, the system further comprises a data collection module arranged to obtain an input signal reflecting a measure of the level of pain experienced by the human subject, and an analyzing module arranged to analyze the input signal reflecting a measure of pain; wherein the analyzing module based on the analysis of the input signal is arranged to perform one or more acts such as to decrease the input signal reflecting a measure of pain until the input signal reflects a target level of pain or optionally when a maximum treatment time has elapsed, wherein the acts are selected from instructing the frequency regulating module to adjust the frequency; instructing the amplitude regulating module to adjust the amplitude; instructing the pressure regulating module to adjust the pressure, or instructing the regulating modules to terminate stimulation in a first nasal cavity and optionally prompt an operator to continue stimulation in a second nasal cavity. The analysis may for example involve, after a predetermined stimulation time period, comparing the measure of pain with the target level of pain, and adjusting at least one of the above mentioned parameters if the target level is not reached. Another alternative can for example consist in comparison of two obtained individual values of the pain measure. A target level of pain may reflect a painless condition, but may also reflect alleviated pain. The analyzing module may instruct the regulating modules to adjust at least one of the frequency, the amplitude, and the pressure. The amount to adjust may be selected using an algorithm implemented as software in the analyzing module. A grid type algorithm would test combinations of vibration parameters within given boundaries, either randomly or systematically, and use the best of these. A derivative search algorithm would identify a direction in a multidimensional parameter space along which the pain level decreases the most and test new parameter sets along this direction. A heuristic search would use previously accumulated and codified knowledge. Heuristics could for example comprise a rule that implies that the amplitude should decrease when the frequency increases in order to keep the power constant. Different combinations of search algorithms are also possible. A further possibility is to store previously obtained data on experienced pain level as a function of vibration stimulation parameters and use this stored data to select suitable adjustments.

In another embodiment, the system further comprises a data processing module arranged to calculate a derivative of the input signal reflecting a measure of pain; wherein the analyzing module is arranged to analyze the derivative and to perform one or more of the acts as defined above. If the treatment is proceeding satisfactorily, i.e. if the pain measure is decreasing and thus the derivative of the measure is negative, nothing has to be changed. Should the pain measure however not decrease in an expected manner, one or more of the above defined acts may be performed.

The analysis may e.g. include comparison of the calculated derivative with a threshold. There is, in another embodiment, thus provided a system wherein the analyzing module is arranged to perform one or more of the above defined acts when either the input signal reflecting a measure of pain pass a first threshold, or when the derivative of the input signal pass a second threshold. The thresholds may e.g. be predetermined, calculated or derived during treatment of a human subject and may be expressed in absolute or relative terms.

One example of a first threshold is a previous value of the pain measure. Thus, the analyzing module may be arranged to compare a previously obtained value of the input signal with a later obtained value of the input signal, and to instruct the regulating modules as defined above if the difference between the later obtained value and the previously obtained value lies within a predetermined threshold tolerance. If the later obtained value is less than the previously obtained value, the pain measure is being reduced and the treatment is effective. If the pain measure is not being reduced as desired, at least one of the regulating modules may be instructed to adjust one of frequency, amplitude and pressure. The threshold tolerance as mentioned above can be defined as the smallest required change in the input signal reflecting a measure of pain for a certain stimulation setting.

The previous and later value can for example be two consecutively obtained values of the input signal. Alternatively, the previously obtained value can, for instance, be defined as the average over the last n number of samples, where n is an integer; as a weighted average over all previously obtained values, or as a function of the previous and later obtained values. The previous value(s) may be stored e.g. in a memory module.

One example of a second threshold is a desired rate of change in the pain measure. If the derivative of the pain measure changes from a negative value to a positive value, i.e. pain is starting to increase, and in doing so pass the second threshold, one of the above defined acts can be performed, such as for examples instructing at least one of the regulating modules to adjust one of frequency, amplitude and pressure.

In yet another embodiment, the analyzing module is arranged to instruct the regulating modules to terminate stimulation in the nasal cavity when either the input signal reflecting a measure of pain falls below a third threshold, or when the derivative of the input is zero or within a derivative tolerance, or optionally when a maximum treatment time has elapsed. The third threshold may thus reflect a pain-free condition or a condition with an acceptable level of pain. The derivative tolerance, on the other hand, should be understood as a tolerance around zero. This represents the attainment of a constant pain measure. Thus, when the pain is either eliminated completely or has reached an acceptable or constant level, the treatment may be terminated. In some instances, the treatment may however be continued for a minimum treatment duration or in a second nasal cavity.

The level of pain as experienced by the patients can be estimated, by the patient herself/himself, using a visual analogue scale (VAS). The human subjects can estimate their pain before, during and after vibration stimulation on a scale from 0 to 10, wherein 0 corresponds to no pain and 10 corresponds to maximal pain. This represents a subjective estimation of the pain. Objective measures of pain are rare. Brown et al however recently demonstrated (PLoS ONE, 6(9): e24124) that functional Magnetic Resonance Imaging (fMRI) scans of the brain can be used to detect pain. The method is based on a computer algorithm that learns how the brain activity looks like when patients feel pain and when they do not. It turns out that brain activity and pain sensation may be sufficiently generic so that a previously unknown individual's pain sensation can be assessed in this way. In the present invention, fMRI may be used for adapting pressure, frequency, amplitude and treatment time in an automated fashion without having to rely on patient input. Thus, in another embodiment, the input signal reflecting a measure of pain is either obtained by fMRI or is an index on a VAS scale.

In one embodiment, the system moreover comprise a pain level indicator arranged to record a pain sensation as experienced by the human subject, wherein said recorded pain sensation is indicated by the human subject and used as the input signal. A subjective estimation of a pain sensation may thus be used as the input signal. Examples of means for recording a pain sensation are a lever or a knob. The system may furthermore comprise an aura indicator arranged to record an aura as experienced by the human subject, optionally comprising a user interface part accepting a graphical representation of the visual field experienced by the human subject, wherein said recorded aura is indicated by the human subject and used as the input signal. It should be understood that means for recording a pain sensation may be the same as means for recording an aura. One example of a means for registering an aura, and optionally a pain sensation, is a computer screen. In one embodiment, the system further comprises a pain location indicator arranged to record a pain location, or several pain locations, as experienced by the human subject, wherein said recorded pain location is indicated by the human subject and used as the input signal. At least one of the pain level indicator, aura indicator and pain location indicator may be comprised in the user interface.

In one embodiment, the input information received by the user interface is selected from the group consisting of: a pain location as experienced by the human subject, a pain sensation level as experienced by the human subject, and amount of time elapsed since start of the headache. In one embodiment, the user interface is arranged to instruct the user to position the at least one stimulation member in the left nasal cavity if the perceived pain location is displaced to the left side of the head or in the right nasal cavity if the perceived pain location is displaced to the right side of the head. Thus, based on the human subject's, or patient's, experienced pain location, the user interface, comprised in the control unit of the system, displays where the stimulation member is to be positioned in order to achieve an effective treatment of the headache disorder.

In a further embodiment the user interface is arranged to display the time evolution of the input signal during the treatment duration.

In one embodiment, the system further comprises at least one expansion member arranged to expand the at least one stimulation member, wherein the at least one expansion member comprises a tubular structure arranged at least partly within the stimulation member, wherein the tubular structure is provided with a plurality of openings arranged for fluid communication with the stimulation member. The tubular structure of the expansion member is provided with a plurality of openings for fluid communication with the interior of the stimulation member. These openings ensure that the stimulation member is expanded accordingly when positioned in the nasal cavity, even if there is an obstruction somewhere along the length of the stimulation member due to the complex anatomy of the nasal cavity. The plurality of openings moreover provides the tubular structure with flexibility which facilitates correct insertion and positioning of the stimulation member in the nasal cavity. The stimulation member is preferably introduced into the nasal cavity in a non-expanded state.

In one embodiment, the expansion member further comprises an elongated structure arranged in fluid communication with the tubular structure, wherein the elongated structure is preferably arranged essentially outside the at least one stimulation member.

In one embodiment, a bending stiffness of the tubular structure in a first direction perpendicular to a longitudinal direction of the tubular structure is different from a bending stiffness in a second direction perpendicular to said first direction and to the longitudinal direction of the tubular structure.

In one embodiment, the tubular structure of the expansion member has one opening at one end, said one opening being arranged freely within and in fluid communication with the stimulation member. A free arrangement of the end opening may facilitate preservation of a smooth surface of the stimulation member, by avoiding protruding parts that may harm the sensitive tissue in the nasal cavity.

In one embodiment, a distance from said end of the tubular structure of the expansion member to an inner wall within the stimulation member is comprised in the range of from approximately 1 to approximately 10 mm. This distance may be essentially unchanged when the stimulation member is expanded. In some examples where the stimulation member is elastic, this distance may refer to the distance to an inner wall of the stimulation member when the stimulation member is arranged in an expanded state, also referred to below as a second state.

In one embodiment, the plurality of openings are distributed along a longitudinal direction of the tubular structure. The plurality of openings may for example be arranged alternately on opposite side portions of the tubular structure along the longitudinal direction, wherein a cross section of the tubular structure perpendicular to the longitudinal direction intersects only one opening on either side.

In one embodiment, the number of openings distributed along a longitudinal direction of the tubular structure is between 4 and 6, such as 5. The openings, which may be circular or elliptic cutouts, may each independently have a size in the range of from approximately 1 to approximately 5 mm. Thus, all openings need not have the same size or shape.

In one embodiment, the system further comprises a visual marking on the stimulation member or on the expansion member indicating a preferred angular orientation of the stimulation member relative the nasal cavity for introduction of the stimulation member into the nasal cavity. Such a visual marking facilitates insertion into the nasal cavity.

In one embodiment, the tubular structure of the expansion member has an outer diameter in the range of from approximately 1 to approximately 5 mm, such as from approximately 2 to approximately 4 mm. A diameter of approximately 5 mm or less may further facilitate introduction into the nostril and nasal cavity and positioning in the posterior part of the nasal cavity.

In one embodiment, the part of said tubular structure being arranged within the stimulation member is between approximately 40 and approximately 60 mm in length. This length of the tubular structure may further facilitate insertion and positioning of the stimulation member in the posterior part of the nasal cavity.

In one embodiment, the elongated structure of the expansion member is tubular and has a diameter that is between 2 to 4 times the diameter of the tubular structure of the expansion member. Thus, the tubular structure, which is the part of the expansion member that will be positioned mainly in the nasal cavity during vibratory stimulation, has a smaller diameter than the elongated structure, which is the part of the expansion member that will be positioned mainly outside of the nasal cavity.

In one embodiment, a part of the elongated structure of the expansion member is arranged within the stimulation member, said part having a length of from approximately 5 to approximately 15 mm. This part of the elongated structure may enclose an ending of the tubular structure, preferably an end portion of the tubular structure. The stimulation member arranged around this part of the elongated structure may preferably expand only to a small extent when the device is in use.

In one embodiment, the at least one retaining portion comprises a part of the elongated structure of the expansion member being arranged within the stimulation member. The retaining portion may thus comprise at least a part of the elongated structure and a part of the stimulation member. This part of the elongated structure may have a size, e.g. a diameter, which enables retaining of the stimulation member in an outer part of the nasal cavity such as the nostril. Alternatively, the elongated structure in combination with an at least partly expanded stimulation member enables retaining in an outer part of the nasal cavity such as the nostril.

In one embodiment, the expansion member comprises at least one channel arranged for fluid communication with the stimulation member, such as for supplying fluid to the stimulation member. In embodiments where the expansion member comprises a tubular structure and an elongated structure, the channel fluidly connects the two structures with each other and with an interior of the stimulation member.

In one embodiment, the at least one expansion member comprises at least one channel arranged for fluid communication with the at least one stimulation member, such as for supplying fluid to the stimulation member.

In one embodiment, the posterior stimulating portion comprises at least one expansion member arranged to expand the at least one stimulation member, wherein the at least one expansion member comprises a tubular structure arranged at least partly within the posterior stimulating portion, wherein the tubular structure is provided with a plurality of openings arranged for fluid communication with the posterior stimulating portion.

In one embodiment, the at least one stimulation member is arranged to impart vibrations to the sphenopalatine ganglion via the anterior part of the nasal cavity and to impart vibrations to the hypothalamus via the posterior part of the nasal cavity.

In other system aspects, there is provided a system for treatment of a headache disorder in a human subject, comprising a device comprising a stimulation member arranged to abut against tissue of the nasal cavity and to impart vibrations to the nasal cavity of the human subject, and at least one of a frequency regulating module arranged to adjust the frequency of the vibrations imparted by the stimulation member of the device to the nasal cavity; an amplitude regulating module arranged to adjust the amplitude of the vibrations imparted by the stimulation member to the nasal cavity, and a pressure regulating module arranged to adjust the pressure at which the stimulation member abuts the tissue of the nasal cavity.

In one embodiment, the system may for example comprise at least two regulating modules selected from a frequency regulating module, an amplitude regulating module and a pressure regulating module. In another example, the system comprises a frequency regulating module, an amplitude regulating module and a pressure regulating module.

In one embodiment of the system aspects, the device is as defined in the following device aspect of the present invention.

It should be understood that the embodiments disclosed in relation to one aspect of the present invention are, where applicable, relevant also to the other aspects of the invention. For example, particular embodiments of the device aspect are also relevant to the system aspect and the other way around.

There is provided, in another aspect of the present invention, a device for treatment of a headache disorder in a human subject, comprising a stimulation member arranged to impart vibrations to the nasal cavity of the human subject such that the headache disorder is treated, wherein the device is connectable to a vibration generating member arranged to bring the stimulation member to vibrate. The device according to the second aspect may be used for treatment of a headache disorder, such as a primary and/or secondary headache disorder, by administration of vibrations to the nasal cavity. The stimulation member of said device is, in one embodiment applicable to both device and system aspects of the present invention, arranged to abut against the tissue of the nasal cavity at at least one pressure of between approximately 20 and 120 mbar. Thus, the stimulation member provides direct contact with the tissue of the nasal cavity. Moreover, the stimulation member can be arranged to abut against the tissue of the nasal cavity at a pressure of between approximately 50 mbar and 120 mbar, such as for example between approximately 70 mbar and 110 mbar, such as for example between approximately 75 mbar and 100 mbar. In one example, a relatively low pressure is exerted on the tissue, e.g. a pressure in the range of between approximately 20 mbar and 50 mbar. In another example, a relatively high pressure is exerted on the tissue, e.g. a pressure in the range of between 70 and 120 mbar. During vibration stimulation with a device according to the second aspect, the pressure may be held constant or may be changed, manually or by a system.

In another embodiment, applicable to device and system aspects of the present invention, the stimulation member is arranged to impart vibrations at at least one frequency of between approximately 40 and 100 Hz to the nasal cavity. Thus, it should be understood that vibration stimulation may be performed at one selected frequency, e.g. 68 Hz, or at several frequencies within a predetermined frequency interval, such as between approximately 50 Hz and 80 Hz, such as between approximately 50 Hz and 75 Hz, such as between approximately 55 Hz and 75 Hz, such as between approximately 60 Hz and 75 Hz. Consequently, during vibration stimulation the frequency may be constant or changed, for example manually or by a system.

In an embodiment applicable to the system and device aspect of the present invention, the device may have an arrangement selected from an arrangement to impart vibrations to the posterior part of the nasal cavity; an arrangement to impart vibrations to the anterior part of the nasal cavity; an arrangement to sequentially impart vibrations to the posterior part of the nasal cavity and the anterior part of the nasal cavity, or an arrangement to simultaneously impart vibrations to the posterior part of the nasal cavity and the anterior part of the nasal cavity. Thus, as described in relation to the system aspect, different structures in the nasal cavity may be subjected to vibratory stimulation in order to affect different treatment targets, e.g. the hypothalamus and the SPG. By affecting different targets, different headache disorders may be more effectively treated.

One example of an arrangement specific for a particular part of the nasal cavity is a stimulation member comprising a stimulating portion arranged to abut against the tissue of a particular part of the nasal cavity and to impart vibrations to that part of the nasal cavity. The stimulating member may thus have a stimulating portion specific for the anterior part or the posterior part of the nasal cavity. When the device has an arrangement allowing sequential stimulation of different parts of the nasal cavity, the stimulating member may have a flexible configuration. Different parts of the stimulating member may be active as stimulating portions while other parts of the stimulating member are in passive configuration.

In another embodiment, the stimulation member is expandable and the device can be arranged in a first state wherein the stimulation member can be introduced into the nasal cavity of a human subject, and a second state wherein the stimulation member is expanded to a volume such that the stimulation member abuts against the tissue of the nasal cavity. In the first state, the stimulation member is arranged in an essentially non-expanded state such as to facilitate introduction into the nostril and nasal cavity of a human being. In the second state, the stimulation member is expanded to a volume such as to provide a direct contact with the surrounding tissue of the nasal cavity. The expansion may for example be provided by an expansion member arranged to expand the stimulation member to the second state. This expansion may be accomplished by means of a fluid supplied to the stimulation member, accordingly arranged to encompass such fluid. Once expanded in the nasal cavity, the stimulation member may be brought to vibrate by means of the vibration generating member. Vibrations may for example be transferred to the tissue by pumping fluid in and out of the stimulation member.

In another aspect of the present invention, there is provided a method for preparing treatment of a headache disorder in a human subject, comprising introducing the stimulation member of a device according to the present invention into a nasal cavity of the human subject;

selecting a treatment area in the nasal cavity;

arranging the stimulation member to abut against the tissue of the selected treatment area, and selecting at least one frequency for vibratory treatment of a headache disorder. Based on theoretical estimations and/or previously collected data from vibration stimulation according to the present invention, the method of preparing treatment may provide e.g. improved positioning of the stimulation member and thereby transferring of vibrations to a selected treatment target. This may result in relatively shorter treatment duration. Thus, the method provides preparation and selection of a treatment regime for a human subject. The preparative method may aim at preparing the first and only round of treatment for a particular patient or a second or further round of treatment. If the method concerns preparing a second or further round of treatment for a particular patient, the data, such as the measure of pain and the parameters used, collected during the previous round of treatment may form basis for selection of parameters for the second or further round of treatment.

The treatment area in the nasal cavity, e.g. anterior and/or posterior part, may be selected such as to make the treatment more effective. A treatment area may be selected such as to maximize stimulation of a particular treatment target, e.g. hypothalamus and/or SPG. In some cases, the treatment area may be selected such that certain parts of the bone structures of the nasal cavity, e.g. parts of the inferior, middle and/or superior conchae, are in contact with the stimulation member. Selection of treatment area may be based on theoretical modeling, knowledge of anatomical details for a particular patient, or on results from a previous round of treatment for the particular patient.

The preparative method may further comprise selecting a first, second or third threshold and/or a derivative tolerance for vibration stimulation. These thresholds and derivative tolerance are defined in the system aspect of the present invention and thus represent levels of pain, or the rate of change of the pain measure, where the stimulation parameters frequency, amplitude and pressure may be adjusted or when the stimulation may be terminated in the first (or second) nasal cavity and optionally continued in a second nasal cavity.

The preparative method may further comprise arranging the stimulation member to abut tissue of the selected treatment area at a pressure of between approximately 20 and 120 mbar, such as for example between approximately 20 and 70 mbar, or between approximately 70 and 120 mbar. Furthermore, the vibration frequency specific for treatment of a headache disorder may be selected from a range between 40 and 100 Hz. Specifically, the selected frequency may lie between approximately 50 and 80 Hz, such as for example between approximately 50 and 75 Hz, such as for example between approximately 60 and 75 Hz.

In another aspect, there is provided a method for treatment of a headache disorder in a human subject, comprising imparting vibrations to the nasal cavity of the human subject. The treatment method thus provides an alternative for patients suffering from various headache disorders, such as primary and secondary headache disorders. For some patients suffering from severe chronic headache disorder such as for example cluster headache, the treatment method as described may constitute the only non-invasive treatment form.

The method for treatment of a headache disorder in a human subject, comprising a) selecting a treatment area in a nasal cavity of the human subject;

b) providing a stimulation member arranged for vibration stimulation of the selected treatment area;

c) introducing the stimulation member into the nasal cavity of the human subject;

d) expanding the stimulation member to exert a pressure on tissue of the selected treatment area; and e) bringing the stimulation member to vibrate in the nasal cavity to impart vibrations to the selected treatment area.

As discussed in connection with other aspects of the present invention, the vibrations may be imparted to a posterior part of the nasal cavity; to an anterior part of the nasal cavity; sequentially to a posterior and an anterior part of the nasal cavity, or simultaneously to a posterior and an anterior part of the nasal cavity. Vibration stimulation in different parts of the nasal cavity may be effective for treating different types of headache disorders and for treating headache disorders having pain components with e.g. different origins in the human body.

In another embodiment, the method further comprises the step of imparting vibrations at at least one frequency selected from the range of approximately 40 to 100 Hz. The method may moreover further comprise the step of exerting a pressure of between approximately 20 and 120 mbar on the tissue of the nasal cavity. Particular sub-ranges of frequencies and pressures are as defined in connection with the other aspects of the present invention.

The pressure exerted on the tissue may be altered during the treatment, such that a first pressure initially is exerted on the tissue and a second pressure subsequently is exerted on the tissue. The pressures may for example be selected from a range of between 20 and 80 mbar or from a range of between 81 and 120 mbar, wherein the first and second pressures are not selected from the same range. Thus, a first pressure may be selected either from a lower pressure range or from a higher pressure range as defined above. Should the first pressure be selected from the lower range, the second pressure may be selected from the higher range. The opposite scenario is equally possible. It should be understood that any suitable number of treatment pressures may be selected;

such as a first, second, third, fourth, fifth, and sixth treatment pressure. Dependent on the progress of the treatment, for example when a pain measure or its derivative is compared to a threshold or a tolerance, a treatment pressure may be changed.

In one embodiment, the method further comprises the step of obtaining an input signal reflecting a measure of a level of pain experienced by the human subject; analyzing the input signal and performing one or more acts to decrease the input signal reflecting a measure of pain, wherein the acts are selected from adjusting a frequency of the vibrations imparted to the nasal cavity; adjusting an amplitude of the vibrations imparted to the nasal cavity; adjusting a pressure exerted on the tissue of the nasal cavity, or terminating vibration stimulation in a first nasal cavity and optionally continuing vibration stimulation in a second nasal cavity. The measure of pain may thus be analyzed at determined points of time or continuously and steps may be taken to (further) reduce the measure of pain if the analysis for example reveals that the pain is not decreasing at all, not decreasing fast enough or that the pain has reached a plateau. Specifically, the method may further comprise calculating and analyzing a derivative of the input signal reflecting a measure of pain; and performing one or more of the acts as defined above. To for instance simplify the analysis, the measure of pain or its corresponding derivative may be compared to a reference value such as a threshold. Thus, in another embodiment, one or more of the acts are performed when either the input signal reflecting a measure of pain pass a first threshold, or when a derivative of the input signal passes a second threshold.

Furthermore, the treatment may be terminated in the nasal cavity when either the input signal reflecting a measure of pain falls below a third threshold, or when the derivative of the input signal is zero or within a derivative tolerance. The thresholds and the tolerances are as defined in relation to the system aspect of the present invention and each represents situations during treatment when something, such as a stimulation parameter, a treatment area or the nasal cavity, has to be changed or terminated.

In one embodiment, adjusting further comprises an adjustment selected from: a random adjustment; an adjustment calculated as a function of an elapsed treatment time, an initial value of the input signal reflecting a measure of pain, and a current value of the input signal reflecting a measure of pain; and an adjustment calculated as a function of a derivative of the input signal reflecting a measure of pain and a time development of the pressure, frequency, and amplitude during the treatment.

The input signal reflecting a measure of pain may for example be obtained by fMRI or be an index on a VAS scale. In addition, the input signal reflecting a measure of pain may be provided by the human subject. This should be understood as the human subject himself/herself in some way indicating the experienced pain sensation, for example by using a lever.

One example of a vibration device for use in the method is a device as disclosed in the device and system aspects of the present invention. Embodiments of the device and system aspect of the present invention are consequently, where applicable, relevant to the method aspect. In particular, the stimulation member may comprise at least one retaining portion and at least one stimulating portion.

In another embodiment, the method further comprises the step of adjusting at least one of the pressure, a frequency and an amplitude of the vibrations, and repeating steps a), d) and e) as defined above. In yet another embodiment, the method comprises bringing the stimulation member to an essentially non-expanded state; removing the stimulation member from the nasal cavity; repeating steps a) to e) as defined above in a second nasal cavity of the human subject.

Stimulation of a specific treatment target may be be advantageous for customizing the treatment of a specific headache disorder. The method may thus, in another embodiment, comprise selecting a treatment target and imparting vibrations to the selected treatment target, wherein the treatment target is selected from hypothalamus and sphenopalatine ganglion.

In one embodiment, said providing of step b) further comprises displaying information in a user interface on a type of stimulation member to use for the selected treatment area.

Examples of different headache disorders that may be treated according to the present treatment method are selected from cluster headache, migraine, tension-type headache and medication-overuse headache.

Further objects and features of the present invention will be apparent from the detailed description and the claims.

BRIEF DESCRIPTION OF THE DRAWINGS

Referring now to the Figures, which are exemplary embodiments, and wherein the like elements are numbered alike:

FIGS. 2A-E are schematic representations each depicting an example of a device according to the device aspects of the present invention;

DETAILED DESCRIPTION OF THE PREFERRED EMBODIMENTS

Embodiments of the present invention will now be described as non-limiting examples and with reference to the Figures.

Figure 1B:
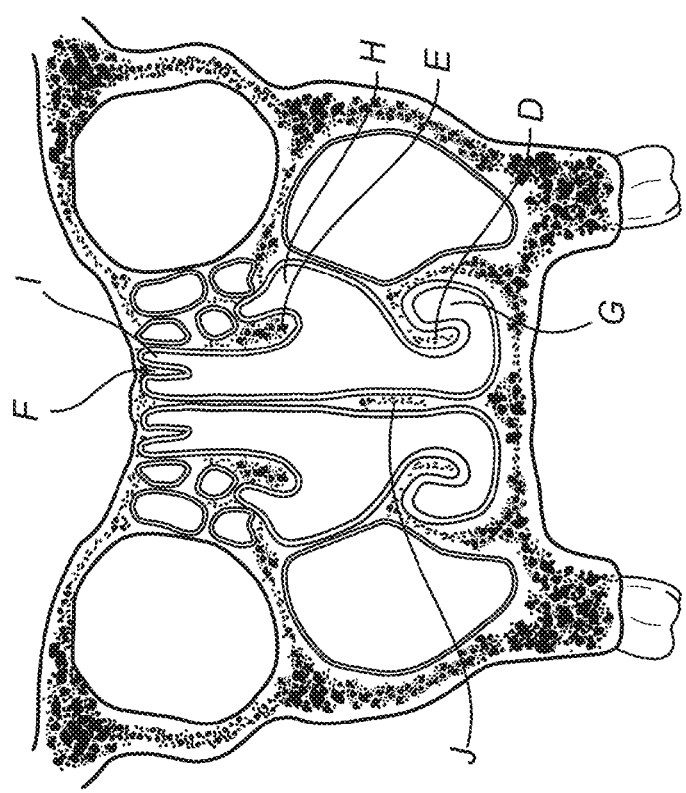
FIGS. 1A and B are schematic representations depicting a side view (A) and a front view (B) of the human nasal cavity(s)
Figure 1A:
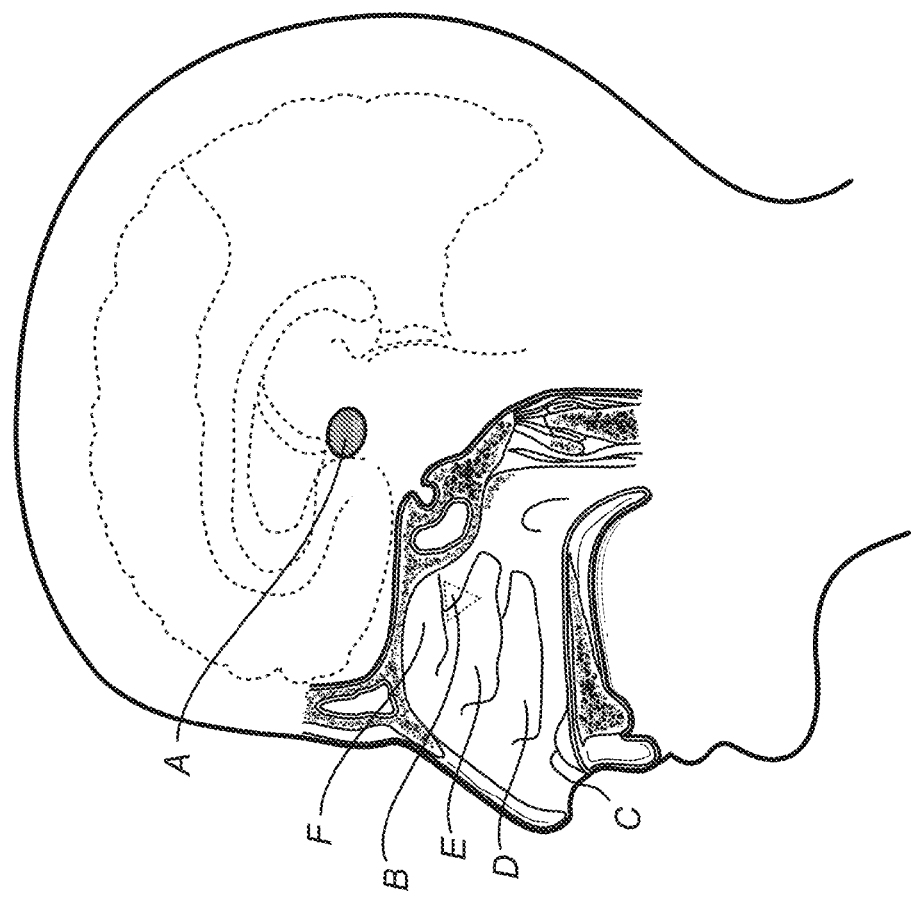

FIG. 1A and FIG. 1B schematically depict the anatomy of the human nasal cavity. FIG. 1A is a side view schematically depicting a nasal cavity of a human and the position of hypothalamus, A, and sphenopalatine ganglion, B, relative one nasal cavity. FIG. 1B schematically depicts the human nasal cavities seen from the front.

The nose has two cavities, separated from one another by a wall of cartilage called the septum, J, as can be seen in the front view of the nasal cavities in FIG. 1B. The vestibule, C, is the most anterior part of the nasal cavity. On the sides of the nasal cavity are three horizontal outgrowths called nasal conchae or turbinates. The conchae are several thin, scroll-shaped bony elements forming the upper chambers of the nasal cavities. They increase the surface area of these cavities, thus providing for rapid warming and humidification of air as it passes to the lungs. The inferior conchae, D, are the largest of the conchae and are responsible for the majority of the airflow direction, humidification, heating and filtering of air inhaled through the nose. The open region defined by the inferior conchae is called the inferior meatus, G. The middle conchae, E, are smaller. They project downwards over the openings of the maxillary and ethmoid sinuses (not shown), and act as buffers to protect the sinuses from coming in direct contact with pressurized nasal airflow. Most inhaled airflow travels between the inferior conchae and the middle conchae. The open regions defined by the middle conchae, E, are called the middle meatus, H. The superior conchae, F, are smaller structures and serve to protect the olfactory bulb. The superior conchae completely cover and protect the nerve axons piercing through the cribriform plate (a porous bone plate that separates the nose from the brain) into the nose. The open regions defined by the superior conchae, F, are called the superior meatus, I.

Each inferior nasal concha, D, is considered a facial pair of bones since they arise from the maxillae bones and projects horizontally into the nasal cavity. Posterior of the inferior nasal conchae are the middle nasal conchae, E, and superior nasal conchae, F, which arise from the cranial portion of the skull. Hence, these two conchae are considered as a part of the cranial bones.

The term anterior part of the nasal cavity as used herein should be understood as the part of the nasal cavity from the nostril to the anterior third of the inferior and middle conchae. The term posterior part of the nasal cavity as used herein should be understood as including at least the posterior two thirds of the inferior and middle conchae.

The communication path between the stimulation member of a device according to the present invention and a specific treatment target, such as e.g. the hypothalamus and/or SPG, is not completely understood. However, a type of sensory receptors called mechanoreceptors is believed to be involved. Mechanoreceptors are responsible for detection and communication of mechanical influence. There are four main types of mechanoreceptors in the human body: Pacinian corpuscles, Meissner's corpuscles, Merkel's discs, and Ruffini corpuscles. Pacinian corpuscles (also known as lamellar corpuscles) detect rapid vibrations (200-300 Hz). Meissner's corpuscles (also known as tactile corpuscles) on the other hand detect changes in texture (vibrations around 50 Hz) and adapt rapidly. Merkel's discs (also known as Merkel nerve endings) detect sustained touch and pressure and adapt slowly. Ruffini corpuscles (also known as Ruffini's end organs, bulbous corpuscles, and Ruffini endings) are slowly adapting receptors that detect tension deep in the skin. Most studies of mechanoreceptors have been performed on the skin. Less is known about how the receptors react in the nasal mucosa or when they are attached to e.g. the cranial bones.

It is conceivable that the frequency content of the vibration stimulation according to the present invention may be fine tuned to match the response of some of the mechanoreceptors in order to obtain a desired therapeutic effect. There is a clear change in patient response when the frequency is varied, which can be interpreted as an excitation of a resonance within the body. Thus, by imparting vibrations within for instance the posterior part of the nasal cavity, the nervous system may be excited at a particular frequency so as to transmit signals to the hypothalamus. Since the middle conchae are attached to the cranial bone a large number of receptors with connections into the brain can be excited by the vibration stimuli.

With reference to FIG. 2A, a specific example of a device according to the device aspects of the invention will now be discussed. The device 1 for treatment of a headache disorder in a human subject comprises a stimulation member 2 arranged in an expanded, second state and an expansion member 3. The stimulation member 2 is arranged to partly surround the expansion member 3, such that the end portion of the expansion member is located inside the stimulation member.

Alternative configurations are however also considered within the scope of the present invention. The stimulation member 2 may for example be connected adjacent to the end portion of the expansion member 3 not shown), and consequently arranged to not essentially enclose the expansion member. In yet another exemplary configuration, the stimulation member may be arranged as a sleeve around the expansion member 3 some distance away from the end portion (not shown).

The stimulation member may be made of a material such that it does not chemically or biologically affect any body tissue with which it comes into contact. Thus, it may have no local effect on body tissue. Non-limiting examples of materials are plastic materials or rubber materials. In some instances, the stimulation member is made of latex.

The stimulation member may furthermore comprise an outer surface that minimizes friction between the stimulation member and the surrounding tissue during introduction into and when positioned in the nasal cavity. The stimulation member may e.g. be constructed from a material providing a smooth outer surface or be coated with a lubricant, such as e.g. a paraffin solution. Further, the material of the stimulation member may be flexible, providing the stimulation member with elastic properties. The size and volume of the stimulation member may consequently vary by an inner pressure. In alternative embodiments, the stimulation member is made up of an inelastic material. In such embodiments, the size of the stimulation member is decreased in the first state of the device wherein the stimulation member is introducible into the nasal cavity. In the second state, the stimulation member is expanded for abutting against tissue surfaces. Furthermore, the stimulation member may have partly elastic properties, which makes it both shrink and fold when returning to the first state of the device. In such cases, the stimulation member may be made of a thin material which can fold.

One non-limiting example of a stimulation member is a balloon, which in an at least partly expanded state establishes a contact surface between the device and parts of the nasal cavity. Other examples of a stimulation member include bags, bubbles and foam devices.

The expansion member 3, e.g. as depicted in FIG. 2A, comprises at least one channel 4 for supply of fluid to the stimulation member. The stimulation member thus comprises a chamber for containing fluid supplied by the expansion member. The chamber walls are defined by the inner surface of the stimulation member. The supply of fluid to the stimulation member via the expansion member thus influences the volume and degree of expansion of the stimulation member. To allow free passage of fluid from the expansion member to the stimulation member, the end portion of the expansion member comprises at least one opening. If the end portion of the expansion member 3 is arranged within the stimulation member 2, as for example depicted in FIG. 2A, the end portion may comprise more than one opening for supply of fluid to the stimulation member 2. The parts of the expansion member 3 and stimulation member 2 in contact with the human body typically define a closed system to prevent leakage of fluid to the human body.

Examples of an expansion member comprising at least one channel include a pipe, a tubing, a conduit, a cylinder, a tube etc. The expansion member may for instance be made of a plastic, rubber or metal material.

The supply of fluid, e.g. a gas or a liquid, may be controlled by an external apparatus via the expansion member. Such an external apparatus may comprise a cylinder with a movable plunger that, by moving back and forth, can regulate the amount of fluid in the cylinder and thereby regulate the amount of fluid in the expansion member.

In embodiments where the device comprises a vibration generating member arranged to bring the stimulation member to vibrate, the vibration generating member may for example comprise a vibration generator controlled by an applied electrical voltage supplied from a control unit. In such examples, the vibration generating member may be arranged within the stimulation member.

In another example, the vibration generating member is externally arranged. Such an external vibration source, for example a transducer, may be arranged so as to supply vibrations to a fluid contained within the stimulation member.

Vibrations may furthermore be imparted to the nasal cavity via the fluid comprised within the stimulation member. Thus, the vibration generating member may provide vibrations to the fluid, which functions as a medium for transferring vibrations via the expansion member to the stimulation member.

The vibratory stimulation in the nasal cavity may be conducted at a frequency of between 40-100 Hz, but other frequencies are also anticipated. The amplitude of the vibrations applied to parts of the nasal cavity may be comprised within the range of between approximately 0.05 mm and approximately 20 mm, such as 0.3 mm and approximately 5 mm, but other amplitudes are also anticipated. It should be understood that the amplitude required for a certain level of pain reduction may also be dependent on the nature of the nasal cavity and the sensitivity of the patient in question.

It should be understood that the device embodiments depicted in e.g. FIGS. 2A-D and 3A-B may be comprised in a system as described herein.

With reference to FIG. 2B, a specific example of a device according to the invention will now be discussed. The device 1 for treatment of a headache disorder in a human subject comprises a stimulation member 2 and an expansion member 3. The stimulation member 2 comprises a stimulating portion 5, which in an expanded second state abuts and imparts vibrations to tissue of the posterior part of the nasal cavity. A retaining portion 6 of the stimulating member is arranged to abut tissue in the anterior part of the nasal cavity. In this example of a device according to the invention, the stimulating portion of the stimulating member may be arranged in a first non-expanded and a second at least partly expanded state, whereas the retaining portion remains in a non-expanded state. While the stimulating portion may consist of a flexible material, the retaining portion may consist of an inelastic, optionally enforced or rigid material. The stimulating portion 5 and the retaining portion 6 are in this case both arranged to at least partly surround the expansion member 3, such that an end portion of the expansion member is located inside the stimulation portion.

The stimulation member may, when it abuts nasal tissue in its expanded state, for instance have a circular, oval or droplet shape, depending on the nasal anatomy of the patient in question.

With reference to FIG. 2C, a specific example of a device according to the invention will now be discussed. The device 1 for treatment of a headache disorder in a human subject comprises a stimulation member 2 and an expansion member 3. The stimulation member 2 comprises a stimulating portion 5, which in an expanded second state abuts and imparts vibrations to tissue of the anterior part of the nasal cavity. A retaining portion 6 of the stimulating member is arranged to abut tissue in the posterior part of the nasal cavity. In this example of a device according to the invention, the stimulating portion of the stimulating member may be arranged in a first non-expanded and a second at least partly expanded state, whereas the retaining portion remains in a non-expanded state. While the stimulating portion may consist of a flexible material, the retaining portion may consist of an inelastic, optionally enforced or rigid material. The stimulating portion 5 and the retaining portion 6 are in this case both arranged to at least partly surround the expansion member 3, such that an end portion of the expansion member is located inside the retaining portion.

With reference to FIG. 2D, an example of a device for treatment of headache disorders by imparting vibrations to the nasal cavity is shown. The device 1 comprises an expandable stimulation member 2 depicted in an at least partly expanded state. The interior 28 of the stimulation member 2 is fluidly connected with an expansion member 3 arranged to expand the stimulation member. The expansion member 3 comprises a tubular structure 24, which may be arranged at least partly within the stimulation member. The tubular structure 24 is provided with a plurality of openings 25 arranged for fluid communication with the interior 28 of the stimulation member 2. The expansion member 3 moreover comprises an elongated structure 26 arranged in fluid communication with the interior 28 of the stimulation member via the tubular structure 24. The elongated structure may be arranged essentially outside the stimulation member 2, or partly inside the stimulation member 2. The elongated structure may enclose a part of the tubular structure 24.

Each end portion of the tubular structure 24 may be provided with an opening for fluid communication with the interior 28 of the stimulation member and the elongated structure 26. Fluid communication may be accomplished through channel 4. The tubular structure 24 may extend within essentially the entire length of the stimulation member 2. In one embodiment, the tubular structure leaves a distance from an end of the tubular structure to an inner wall of the stimulation member of 5 mm. The circumferential surface of the end portion of the tubular structure 24 is however distanced from the inner walls of the stimulation member.

An end portion 27 of the elongated structure 26 arranged adjacent to the stimulation member 2, or arranged within the stimulation member, may function as a retaining portion when the device is inserted into the nasal cavity of a human subject. Such an end portion 27 of the elongated structure 26 may be inserted into the nostril of the human subject.

Figure 3:
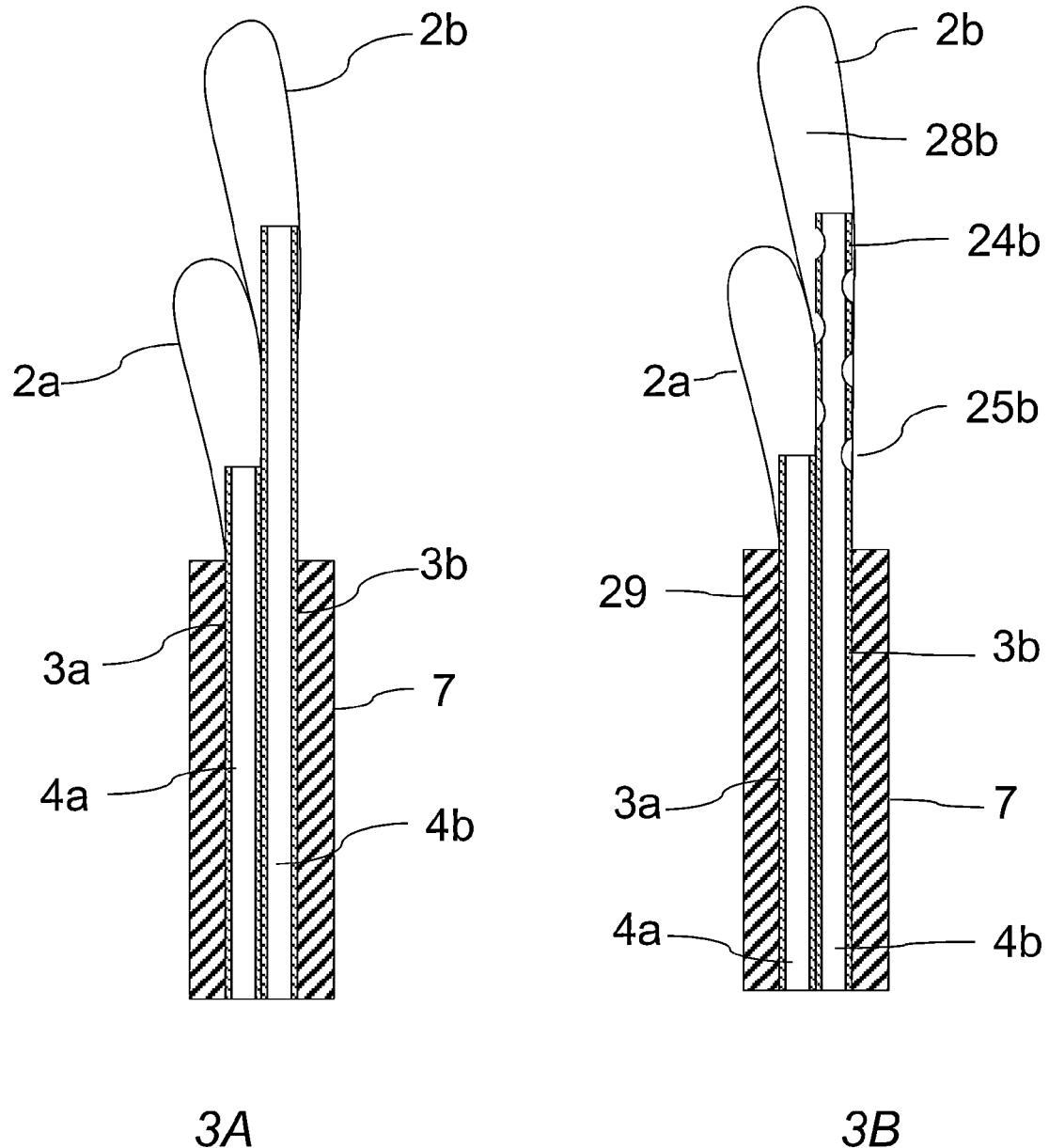
FIGS. 3A and B are schematic representations depicting examples of a device according to the device aspects of the present invention.

With reference to FIG. 3A, yet another specific example of a device according to the present invention will be described. The device 1 has an arrangement specific for sequential administration of vibrations to the posterior and anterior part of the nasal cavity. Thus, the device comprises two stimulating members 2a and 2b, one anterior stimulating member 2a arranged to impart vibrations to the anterior part of the nasal cavity, and one posterior stimulating member 2b arranged to impart vibrations to the posterior part of the nasal cavity. Alternatively, the stimulation members 2a and 2b may be denoted as an anterior stimulating portion and a posterior stimulating portion of a common stimulation member. Each stimulation member is connected to an expansion member 3a and 3b for expanding the stimulation member. Each expansion member 3a and 3b comprises a channel 4a and 4b for supply of fluid such as air to the stimulating members 2a and 2b. The stimulating members thus defines a chamber for comprising such fluid. The expansion members 3a and 3b may be comprised within a common housing 7 that partly or completely covers the expansion members. The housing 7 may function as a stopper that prevents the stimulation members from being inserted too far into the nasal cavity, provided that the outer diameter of housing 7 is larger than the nostril opening. The stimulating members 2a and 2b are alternately brought to vibrate, essentially as described in connection with the other examples of devices, such that vibrations alternately or simultaneously are imparted to tissue of the anterior and posterior parts of the nasal cavity. A hygienic cover (not shown) may optionally be provided for covering both stimulating members. A common cover for the two stimulation members might also make it easier to insert into the nasal cavity.

The device according to FIG. 3A may, in another embodiment, be used for simultaneous administration of vibrations to an anterior and a posterior part of the nasal cavity.

In FIG. 3B, yet another specific example of a device according to the present invention will be described. The device 1 of FIG. 3B resembles the embodiment depicted in FIG. 3A, in that it comprises two stimulating members 2a and 2b, one anterior stimulating member 2a arranged to impart vibrations to the anterior part of the nasal cavity, and one posterior stimulating member 2b arranged to impart vibrations to the posterior part of the nasal cavity. Each stimulation member is connected to an expansion member 3a and 3b for expanding the stimulation members 2a and 2b. The expansion member 3b connected to the posterior stimulating member 2b however comprises a tubular structure 24b, which may be arranged at least partly within the stimulation member 2b. The tubular structure 24b is provided with a plurality of openings 25b arranged for fluid communication with the interior 28b of the stimulation member 2b. The tubular structure 24b may, together with the expansion member 3a, be enclosed in a common housing 7. In one embodiment, the tubular structure 24b leaves a distance from an end of the tubular structure to an inner wall of the stimulation member 2b of 5 mm. The end portion of the tubular structure 24b is distanced from the inner walls of the stimulation member 2b.

The tubular structure 24 and 24b as depicted in FIGS. 2D and 3B is sufficiently resilient to allow for insertion and positioning in the, sometimes irregular, shape of posterior part of the nasal cavity. This is particularly important for movements in the sagittal plane since the stimulation member must pass in a vertical bend through the vestibule. At the same time, the tubular structure must provide sufficient stiffness in order to avoid accidental bending during introduction into the posterior part of the nasal cavity. The tubular structure has a sufficient inner diameter in order to avoid excessive flow resistance, which might cause damping out of vibrations before reaching the stimulation member. Furthermore, the tubular structure may have a wall thickness that in combination with the plurality of openings achieves a suitable stiffness. Other material and mechanical properties may also have an influence on the stiffness of the tubular structure.

An end portion of the tubular structure, 24 and 24b as depicted in FIGS. 2D and 3B, arranged within the stimulation member 2b may be rounded or beveled to prevent the device from getting stuck when introduced into the nasal cavity and to minimize any discomfort for the patient.

An end portion 29 of the common housing 7 depicted in FIGS. 3A and 3B arranged adjacent to the two stimulation members may function as a retaining portion when the device is inserted into the nasal cavity of a human subject. Such an end portion 29 of the common housing may be inserted into the nostril of the human subject.

In an embodiment wherein the openings are provided on alternating side portions of the tubular structure 24 and 24b, it may be advantageous to provide a visual marking, for example a visual marking 32 as depicted in FIG. 2E, on the device to facilitate and ensure insertion in the correct angular orientation.

Figure 4A:
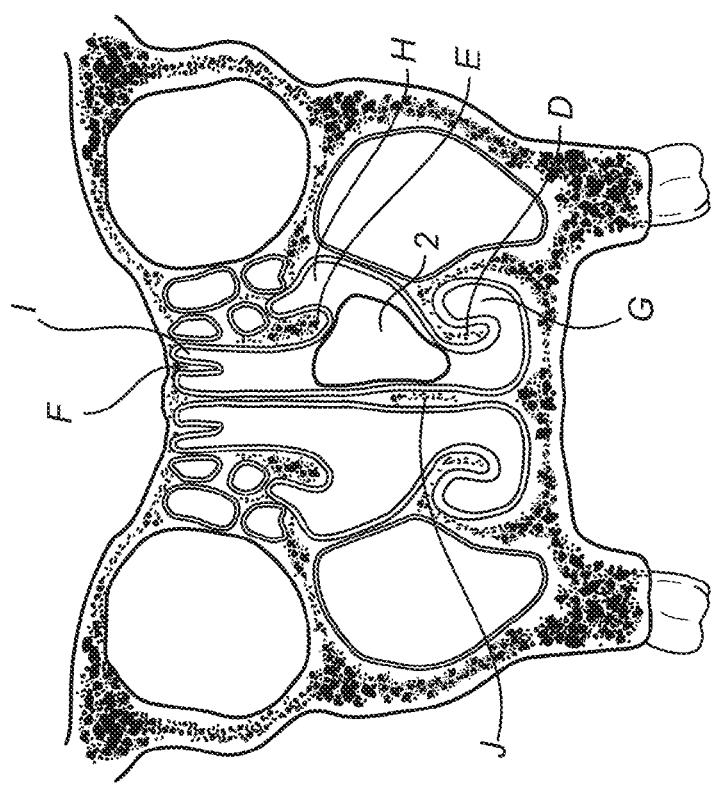
FIGS. 4A and B are schematic representations depicting one example of a device according to the device aspects of the present invention positioned within the nasal cavity of a human subject, seen from the side (A) and from the front (B)
Figure 4B:
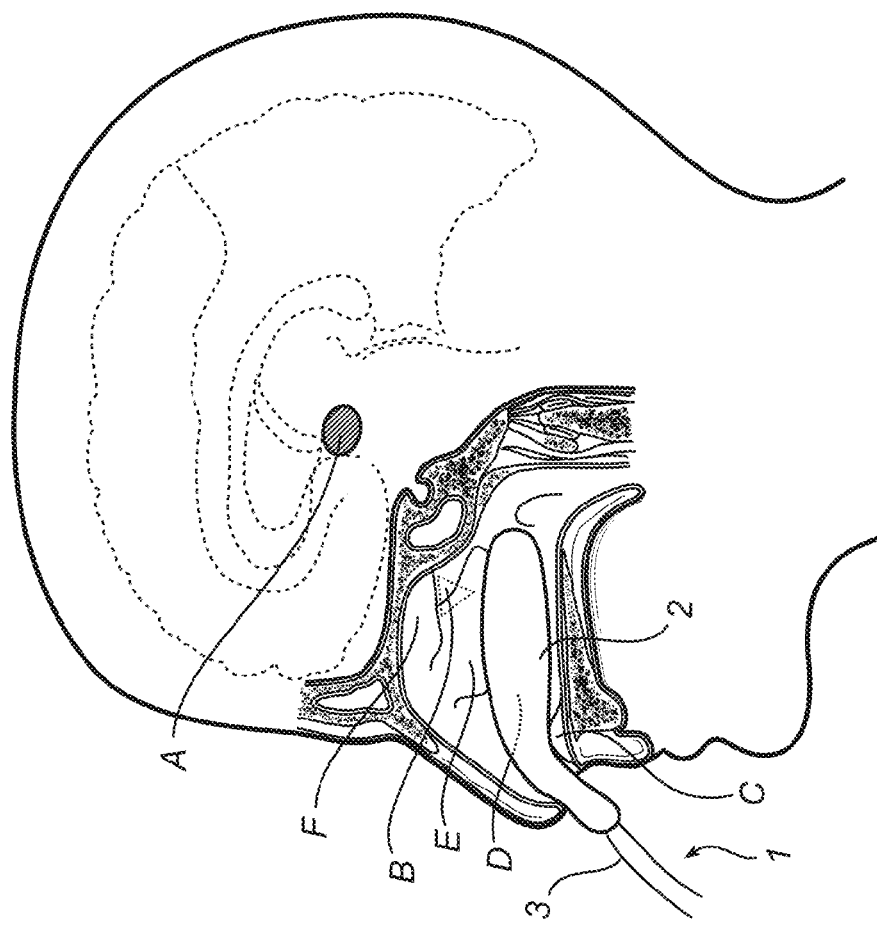

In FIG. 4A, the stimulation member 2 of the device 1 is in an at least partly expanded state positioned within the nasal cavity. An expansion member 3 is partly located within the stimulation member 2 and partly located outside of the nasal cavity during vibration stimulation. The expansion member 3 accordingly provides expansion of the stimulation member 2 to a size and/or volume which is suitable for stimulation. Such expansion may be achieved by supply of fluid to the stimulation member through one or more channels, which are comprised in the expansion member. The volume of fluid supplied to the stimulation member in turn influences the inner pressure of the stimulation member and consequently the pressure exerted on the surrounding tissue. Treatment of a headache disorder by imparting vibrations to (specific parts of) the nasal cavity is initiated when the stimulation member has obtained satisfactory contact with the tissue of the nasal cavity.

The dimensions of the stimulation member or, where applicable, the stimulating portion, may evidently be adapted to the size and shape of the nasal cavity of the patient to be treated. The length of the stimulation member when located within the nasal cavity may vary between approximately 3 mm to approximately 100 mm, for example from 40 to approximately 60 mm, for a Caucasian adult. When the patient on the other hand is a newborn baby, the length of the stimulation member when located within the nasal cavity may be from approximately 3 mm to approximately 20 mm. It should be understood that the actual length of the stimulation member when positioned within the nasal cavity is dependent on the degree of expansion of the stimulation member and the size of the nasal cavity. A stimulating portion of a stimulating member may e.g. have a length of 25 mm when positioned within the posterior part of the nasal cavity.

The lateral width of the stimulation member or, where applicable, the stimulating portion, when positioned in the nasal cavity may for instance vary from approximately 1 mm to approximately 40 mm, such as from approximately 10 to approximately 20 mm for an adult, depending on the degree of expansion of the stimulation member or the stimulating portion and the size of the nasal cavity. When positioned in the nasal cavity of a newborn, the stimulation member or stimulating portion may be approximately from 1 to approximately 3 mm wide. It is understood that, depending on the patient to be treated, the dimensions of the stimulation member or stimulating portion may vary outside of the ranges given above.

In certain aspects of the present invention, a plurality of geometrically different stimulation members is provided. Such a plurality may for instance be provided in a kit of different stimulation members, wherein each of the stimulation members differs from the others in e.g. length and lateral width. A plurality of stimulation members may be defined as comprising two, three, four, five, or more stimulation members having different dimensions and shape, for example within the ranges as disclosed above. The stimulation members may exhibit different laterally curved and bent forms to facilitate insertion and positioning.

To render possible a smooth and painless introduction into the nasal cavity, the width of the stimulation member or the stimulating portion may, when arranged in the first state, not exceed the width of the nostril of the patient to be treated. In newborns, for instance, the stimulation member or the stimulating portion may, in its first state, be approximately 1 mm wide. To further facilitate the introduction of the stimulation member into the nasal cavity it may be preformed with a slight bend to better fit the nasal anatomy.

The device according to the present invention may conveniently comprise a safety valve, which, in case the pressure within the stimulation member exceeds a certain maximum value, can release some of the pressure, for example by releasing fluid from the stimulation member.

To further facilitate insertion and positioning within the nasal cavity, the device may be provided with a scale to aid the person performing the stimulation. The expansion member may for example be provided with such a scale, which, together with any prior knowledge of the particular patient's anatomy may indicate how far into the nasal cavity the device has been inserted. Alternatively, the device may be provided with a stop bigger than the nostril to prevent the stimulation member from being inserted too far into the nasal cavity.

In other embodiments, the device is provided with anchoring means to prevent the device from unintentionally moving during the stimulation in the nasal cavity. Anchoring means may be provided in the form of a helmet, facial mask or a headband. Such anchoring means keep the stimulation member in constant position relative to the nasal cavity even if the patient moves his/her head during the stimulation or if some other disturbance occurs. One example of an anchoring means, or anchoring member 30, is depicted in FIG. 6.

In embodiments where the stimulation member comprises a stimulating portion arranged to abut against the tissue of the anterior and/or posterior part of the nasal cavity and to impart vibrations to tissue in those parts of the nasal cavity, a retaining portion may function as anchoring means.

Figure 5:
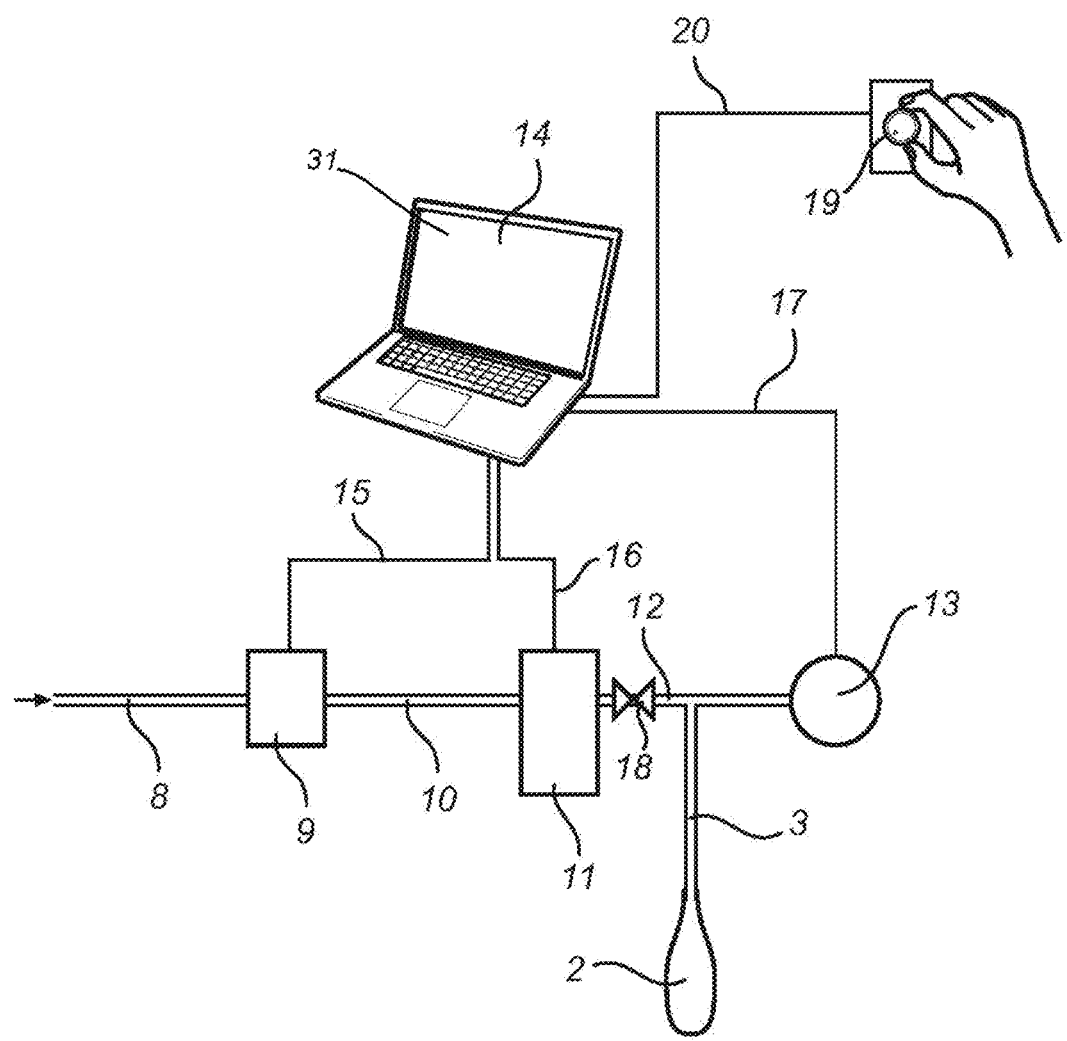
FIG. 5 is a schematic view depicting an example of a system according to the system aspect of the present invention.
Figure 6:
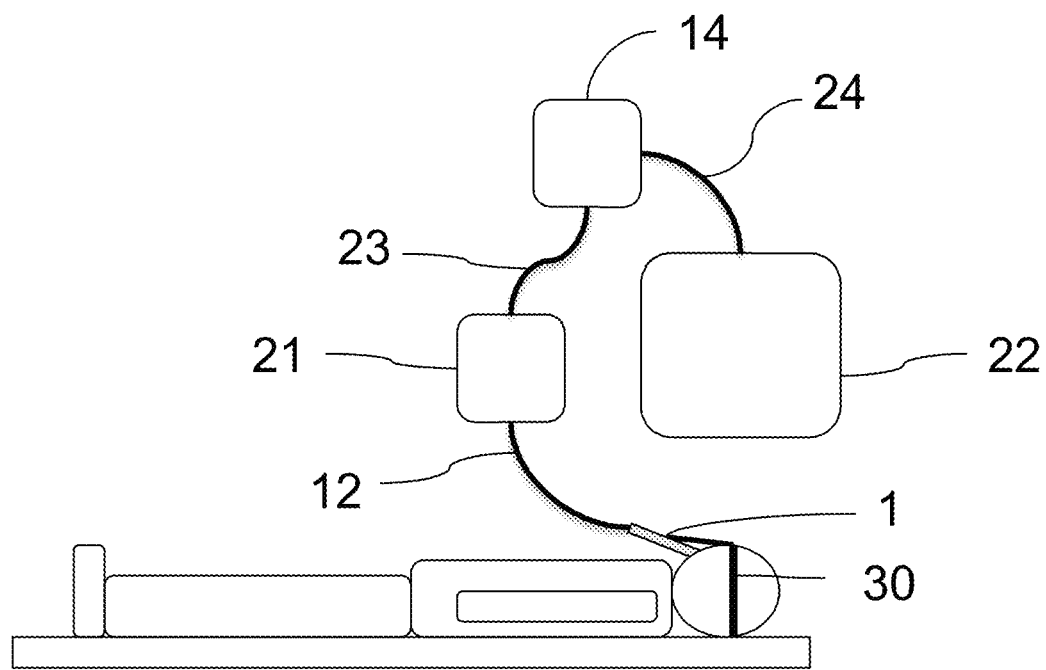
FIG. 6 is a schematic view depicting an example of use of a system according to the system aspect of the present invention.

With reference to FIGS. 5 and 6, specific examples of a system according to the system aspect of the invention will now be discussed.

The system of FIG. 5 comprises device 1, having a stimulation member 2 and expansion member 3 as described above. The device may be secured around the patient's head by an anchoring means 30, for example provided as a headband. Fluid such as air enters the system via inlet 8. In the pressure regulating module 9, e.g. a pressure pump, the fluid is pressurized before being supplied to a frequency and amplitude regulating module 11 via tubing 10. The frequency and amplitude regulating module, e.g. an oscillation pump, provides vibrations having a desired frequency and amplitude to the pressurized fluid which, via tubing 12 and expansion member 3, is supplied to the device 1. The system pressure is monitored by a pressure sensor 13, such as a manometer. Alternatively, the pressure sensor could be integrated in the pressure regulating module or the frequency and amplitude regulating module.

The control unit 14 receives input via line 15 from the pressure regulating module 9, via line 16 from the frequency and amplitude regulating module 11 and via line 17 from the pressure sensor 9. The control unit further controls the pressure regulating module 9 via line 15 and the frequency and amplitude regulating module 11 via line 16. Embodiments where the control unit 14 does not receive input from any one of or all of the regulating modules and sensor, but only outputs instructions to the regulating modules, are also within the scope of the present invention.

The system is further provided with safety valve 18, arranged to release fluid from the system should the system pressure get too high.

The system further comprises a pain level indicator such as a lever or a knob 19 connected to the control unit 14 by line 20. The patient subjected to treatment with a system according to the invention utilizes the knob 19 for indicating the level of pain experienced before, during and/or after treatment. Thus, the input signal reflecting a measure of pain may be provided to the control unit 14 by means of the knob 19. As an example, the settings of the knob correspond to pain levels on a VAS scale.

Alternatively, the pain level may be indicated on e.g. a computer screen, for example a computer screen 31 comprised in the control unit 14. The computer screen is thus an example of an aura indicator arranged to record an aura as experienced by a patient, and it comprises a user interface part accepting a graphical representation of the visual field experienced by the patient. This recorded aura as indicated by the patient may be used as the input signal in the system. Migraine patients experiencing an aura, i.e. diminished field of view, before and during the attacks, may for example indicate on the screen the (changing) size of the aura during treatment.

In this case the patient may further show which part(s) of the head that is (are) affected, either by using a touch screen, a joy stick, a mouse, a computer screen 31 or some other pointing device. These constitute examples of pain location indicators, which are arranged to record a pain location as experienced by the patient. This recorded pain location is indicated by the patient and used as the input signal in the system. The control unit 14 may moreover comprise a data collection module arranged to collect input from the above mentioned regulating modules and sensor. The data collection module may moreover obtain an input signal reflecting a level of pain experienced by the patient. Thus, control unit 14 may receive an input signal reflecting a measure of pain from a monitoring device (22, FIG. 6), such as a functional neuroimaging device.

One example of a control unit is a microprocessor comprising suitable peripheral I/O capability executing software e.g. for analyzing the input signal and to determine how to adjust e.g. any of the frequency, the amplitude and the pressure. It is contemplated that other types of control units may be used, such as e.g. a personal computer.

An analyzing module (not shown) may moreover be comprised within the control unit. Such an analyzing module provides analysis of the data collected from the separate parts of the system, where applicable from the devices, lever, modules and/or sensor of the system. The analyzing module may for example compare a previously collected value of the input signal with a later collected value of the input signal, and subsequently compare the difference between the two with a predetermined threshold tolerance.

In other examples of a system, a data processing module (not shown) is comprised within the control unit. The data processing module provides calculations of the collected input signal and of e.g. thresholds. Based on analysis of processed data, such as the derivative of the input signal reflecting a measure of pain, the analyzing module is arranged to instruct any one of the regulating modules that may be present in the system to adjust e.g. the frequency, the amplitude and/or the pressure. It should be understood that the analyzing module may instruct the regulating modules in such a manner that the treatment is terminated. The derivative of the measure reflects the rate of change of the measure and may thus indicate for example when adjustment of the above mentioned parameters should be made in order to achieve a change in the measure, and in addition when no more changes in the measure can be expected and stimulation consequently should be terminated.

Thus, when a second threshold of the pain measure is reached, e.g. as represented by the derivative being zero or close to zero, the analyzing module may be arranged to instruct the frequency regulating module, the amplitude regulating module and the pressure regulating module to adjust the frequency and/or the amplitude to zero and the pressure to reflect atmospheric pressure.

Other thresholds may moreover be determined. One example of another threshold may be expressed as a function of both the measured value and its rate of change. For example, if the rate of change is sufficiently small and the measured value is considered as high the analyzing module proposes continued treatment in a second nasal cavity. One example of such a threshold is $tol_2$ in FIG. 8B.

The analyzing module may moreover be arranged to terminate stimulation dependent on stimulation time. A maximum stimulation time can be defined after which the stimulation is terminated irrespective of which activity level has been attained (see e.g. $t_{max}$ in FIG. 8). A minimum stimulation time can defined as the shortest time interval during which vibrations are administered (e.g. $t_{min1}$ in FIG. 7). Having a minimum stimulation time may be advantageous, since any unstable readings in the beginning of a stimulation period may be disregarded. In the case where vibration stimulation in both nasal cavities is desired, the minimum stimulation time corresponds to the stimulation time in a first nasal cavity before switching nasal cavity (e.g. $t_{min2}$ in FIG. 7) or the minimum stimulation time for each nasal cavity. Another example is to continue stimulation for a predetermined minimum stimulation time ($t_{min}$) after the pain measure has passed a first threshold (see FIG. 8C).

In another example, the system further comprises a memory module (not shown, may e.g. be integrated within the control unit) arranged to store at least one previously obtained value of the input signal. The memory module is arranged to either store several previous individual values of the input signal, or to successively replace a previous value of the input signal each time the data collection module obtains a new signal, but after the above defined analysis has been made.

FIG. 6 demonstrates vibration stimulation in the nasal cavity of a human patient with an exemplary system according to the invention. A device 1 is positioned within the nasal cavity of the patient. The stimulation member is expanded to a second state such that it abuts parts of the nasal cavity. A regulating module 21 for regulation of one or more of pressure, vibration frequency and amplitude is connected to the device 1 via tubing 12. When imparting vibrations to the posterior part of the nasal cavity, pain sensation is monitored by monitoring device 22. The monitoring device 22 may provide real-time monitoring of a direct or indirect measure correlated to pain sensation, such as for example whole-brain patterns of activity. One example of a monitoring device is an fMRI instrument.

Control unit 14 receives an input signal reflecting a measure of pain via line 24 from the monitoring device. The control unit 14 comprises a data collection module (not shown) for obtaining the signal. An analyzing module (not shown) and a data processing module (not shown) may moreover be provided within the control unit. The control unit 14 receives information on vibration parameters from the regulating module via line 23. The control unit may via the same line 23 output instructions for controlling the regulating module 21. Such instructions are based on analysis of the input signal obtained from the monitoring device and aims at adjusting any one of the parameters of pressure, vibration frequency or amplitude. In certain instances, when the input signal reflecting a measure of pain reaches a threshold, the control unit may instruct the regulating module to terminate the stimulation and optionally continue the stimulation in a second nasal cavity.

Figure 7:
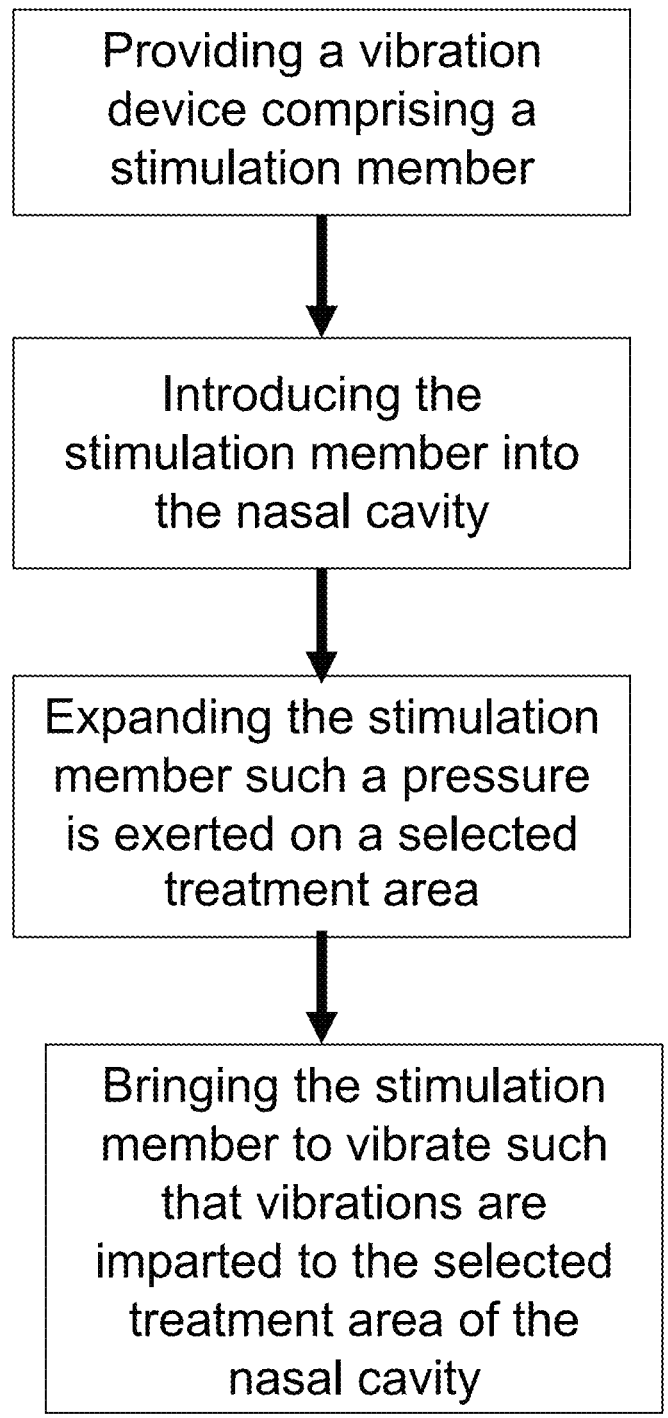
FIG. 7 is a flow chart indicating the steps comprised in one embodiment of a method for treatment of a headache disorder according to the present invention.

A method for treatment of a headache disorder by vibration stimulation in the nasal cavity is exemplified below with reference to FIG. 7.

A vibration device comprising a stimulation member is provided. The stimulation member is via the nostril introduced into the nasal cavity of a patient. The device is thus in a first, essentially non-expanded state when introduced in order to facilitate passage through the nostril and to minimize the risk of frightening the patient by presenting a bulky instrument. A treatment area is selected in the nasal cavity, e.g. an anterior part or a posterior part of the nasal cavity. When positioned adequately, the stimulation member is expanded to a second state such that a pressure is exerted on the tissue of the selected treatment area.

It is to be understood that the volume of the stimulation member may be adjusted to the size of the nasal cavity such that a good contact is achieved with the body tissue prior to vibration stimulation. A good and/or close contact refers to such a contact that the available outer surface of the stimulation member in a second, at least partly expanded, state essentially abuts against the surface of the tissue.

Subsequently, the stimulation member is brought to vibrate such that vibrations are imparted to the selected treatment area of the nasal cavity. The pressure exerted on the selected treatment area may for example initially be relatively high, such as between approximately 71 and 120 mbar. After a predefined period of stimulation at a relatively high pressure, the pressure may be lowered, for example to a relatively lower pressure such as between approximately 20 and 70 mbar, and/or the treatment area may be changed.

When the pain is eliminated or reduced to an acceptable level, stimulation is suitably terminated. The at least partly expanded stimulation member is suitably returned to an essentially non-expanded first state before it is removed through the nostril. Contraction of the stimulation member may for instance be achieved by reduction of fluid pressure within the stimulation member by removal of fluid through the expansion member. When the stimulation member is adequately contracted to an at least partly non-expanded state, the stimulation member may be removed from the nose by the patient himself/herself or by assisting personnel.

It is contemplated that vibration stimulation may be performed with at least one stimulation member in at least a first nasal cavity of the human subject. For example, one device according to the first aspect may be used for single stimulation in one nasal cavity only or for sequential stimulation in both nasal cavities. In another example, two devices according to the first aspect may be used for simultaneous vibratory stimulation in both nasal cavities. It should be understood that pressure and vibration frequency may be the same or different for sequential and/or simultaneous stimulation in both nasal cavities. Two different vibration frequencies with a phase and/or amplitude difference may be applied during simultaneous stimulation to achieve an interference effect.

Prior to stimulation, the method may involve selecting from a plurality of devices comprising stimulation members having individually different geometry a device comprising a stimulation member having a geometry suitable for a specific treatment area within the nasal cavity of a particular human subject. As previously discussed, certain patients might require a stimulation member having a certain shape, length and width/diameter.

In addition, a treatment duration suitable for the patient in question may be selected prior to initiating the stimulation in the nasal cavity. Such selection may comprise selecting a minimum duration for standard stimulation, such as at least 5 minutes in total. Alternatively, the treatment duration may be defined as the period of treatment after the measure of pain has fulfilled a predetermined requirement. Such as after the first threshold is reached, stimulation may continue for yet another 2-5 minutes. Other treatment regimens involve selecting a duration of treatment in a first and/or second nasal cavity.

The method for treatment of a headache disorder may suitably be performed preventive or acute. Patients suffering from a primary headache disorder or a secondary headache disorder may benefit from vibration treatment according to the present invention. Examples of primary headache disorders include, but are not limited to, migraine with and without aura; tension-type headache including infrequent episodic tension-type headache, frequent episodic tension-type headache and chronic tension-type headache; cluster headache and other trigeminal autonomic cephalalgias including other primary headaches. Examples of secondary headache disorders include, but are not limited to, headache attributed to head and/or neck trauma including chronic post-traumatic headache; headache attributed to cranial or cervical vascular disorder including headache attributed to subarachnoid haemorrhage and headache attributed to giant cell arteritis; headache attributed to non-vascular intracranial disorder including headache attributed to idiopathic intracranial hypertension and headache attributed to intracranial neoplasm; headache attributed to a substance or its withdrawal including carbon monoxide-induced headache, alcohol-induced headache, medication-overuse headache including Ergotamine-overuse headache, Triptan-overuse headache and analgesic-overuse headache; headache attributed to infection including headache attributed to intracranial infection; headache attributed to disorder of homoeostasis; headache or facial pain attributed to disorder of cranium, neck, eyes, ears, nose, sinuses, teeth, mouth or other facial or cranial structures including cervicogenic headache and headache attributed to acute glaucoma; headache attributed to psychiatric disorder; neuralgias and other headaches including cranial neuralgias, central and primary facial pain and other headaches including trigeminal neuralgia and other headache, cranial neuralgia, central or primary facial pain.

With reference to FIG. 8A-D, specific examples of stimulation procedures according to the system and method aspects of the present invention will be discussed. FIG. 8A-D represent examples of how stimulation may be conducted and controlled.

Figure 8A:
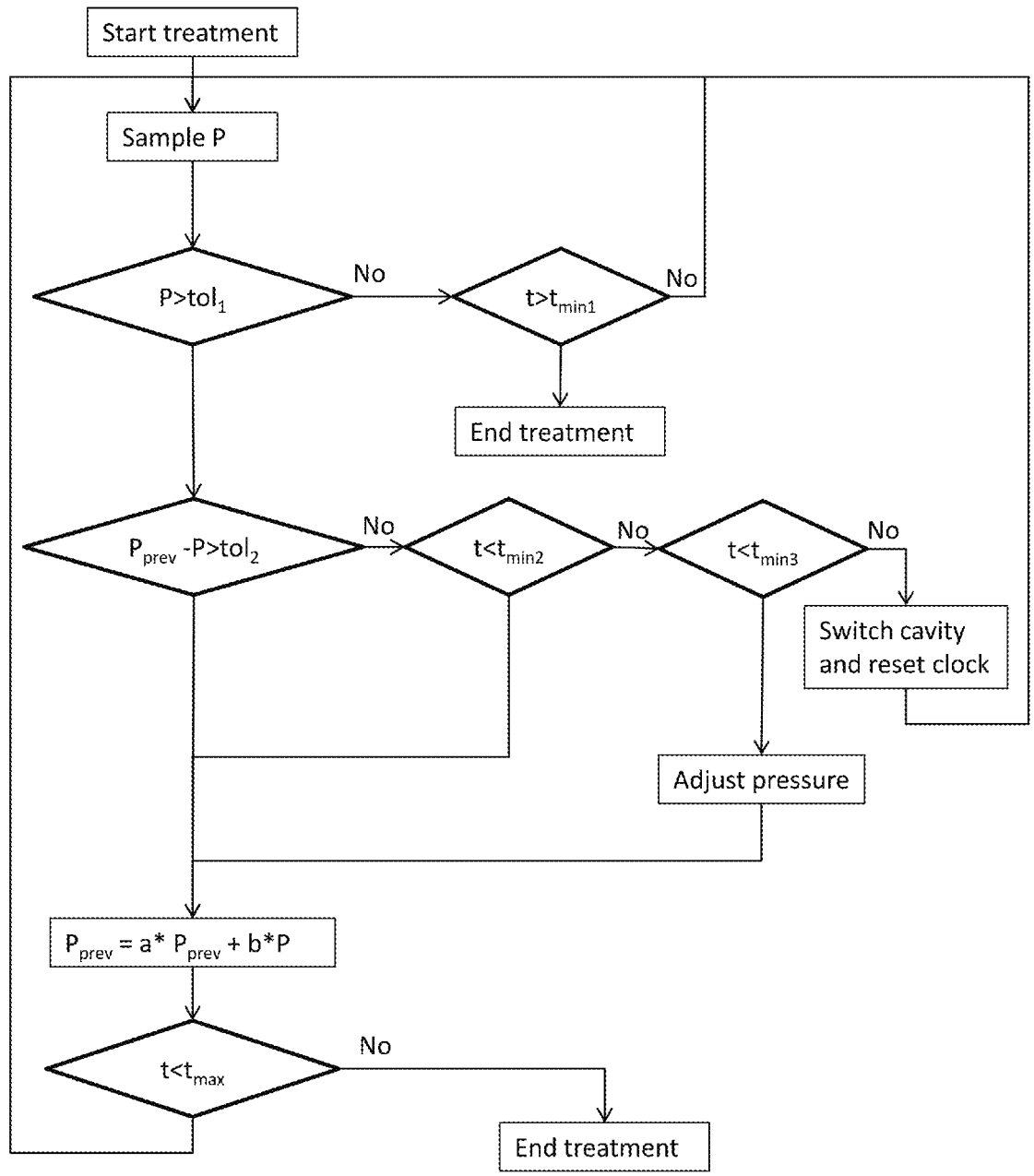
FIGS. 8A-D are flow charts showing examples of treatment procedures according to the system and method aspects of the present invention.

In the procedure of FIG. 8A, an input signal reflecting a pain measure (P) is collected after the treatment has been initiated. If the pain measure P has been decreased to an acceptable level such that it does not surpass a first boundary value ($tol_1$), and the treatment duration surpasses a minimum treatment time ($t_{min1}$), the treatment may be terminated. If the minimum treatment time ($t_{min1}$) has not been reached, treatment is continued and a new pain measure may be collected and analyzed. The first boundary value $tol_1$ is an example of the third threshold as disclosed in the present application.

If the pain measure P has not decreased to an acceptable level, i.e. it still surpasses a first boundary value ($tol_1$), the change in the pain measure in relation to a previous pain measure ($P_{prev}$) is compared to a second boundary value ($tol_2$). If the reduction in pain measure P is satisfactory compared to the previous measure, i.e. if $P_{prev}-P>tol_2$, then two things are done. First, the previous pain measure $P_{prev}$ is updated in a way to make sure that it is not a single deviating value given unreasonable weight in the analysis ($P_{prev}=a*P_{prev}+b*P$). This value of $P_{prev}$ will be used during the next cycle. Secondly, the treatment duration is compared to a maximum treatment time ($t_{max}$). If the maximum treatment time is not reached, the treatment may continue and a further pain measure may be collected in a further cycle of the treatment procedure. If the maximum treatment time on the other hand is reached, the treatment is terminated.

Should however the comparison $P_{prev}-P>tol_2$ show that the current pain measure is not reduced in relation to the previous measure, then, provided that a second minimum treatment time ($t_{min2}$) is not reached, the previous pain measure is updated as described above. If the second minimum treatment time ($t_{min2}$) is reached, but not a third minimum treatment time ($t_{min3}$), the pressure exerted on the nasal cavity is adjusted. If, on the other hand, the third minimum treatment time ($t_{min3}$) is reached, treatment is terminated in a first nasal cavity and continued in a second nasal cavity. When treatment is initiated in the second nasal cavity, the clock is reset and a new cycle of the treatment procedure starts.

Figure 8B:
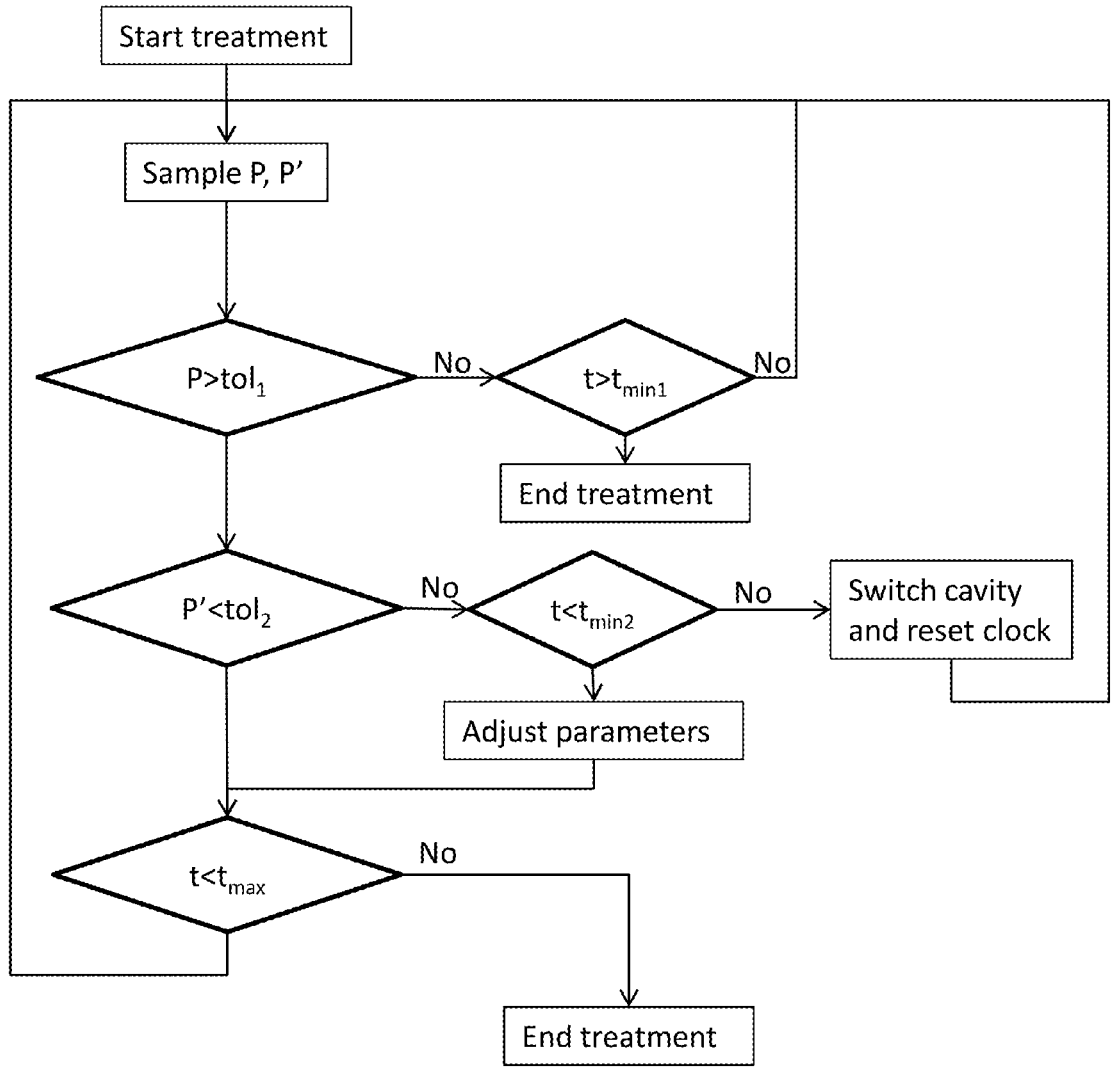

In FIG. 8B, which demonstrates another example of a treatment procedure, both a pain measure (P) and its derivative (P') are collected and calculated when initiating a treatment cycle. The pain measure P is compared to a first boundary value ($tol_1$) in similarity with the procedure of FIG. 8A. If the pain measure P has been decreased to an acceptable level such that it does not surpass a first boundary value ($tol_1$), and the treatment duration surpasses a minimum treatment time ($t_{min1}$), the treatment may be terminated. If the minimum treatment time ($t_{min1}$) has not been reached, treatment is continued and a new pain measure may be collected and analyzed in a further treatment cycle.

If the pain measure P has not decreased to an acceptable level, i.e. it still surpasses a first boundary value ($tol_1$), the derivative of the pain measure (P') is compared to a second boundary value ($tol_2$). If the treatment is having the desired effect, then the derivative of the pain measure should be negative. Thus, if the derivative (P') is smaller than the second boundary value ($tol_2$), the treatment may either continue in a further cycle or be terminated, depending on whether the maximum treatment time ($t_{max}$) has been attained or not. The second boundary value ($tol_2$) is one example of the second threshold as disclosed herein.

A treatment not having the desired effect is reflected in the derivative exceeding the second boundary value ($tol_2$). In such a case, the stimulation parameters such as pressure, frequency, amplitude and treatment area may be adjusted provided that a second minimum treatment time ($t_{min2}$) has not been reached. Should the second minimum treatment time ($t_{min2}$) already be reached, the treatment may be terminated in the first nasal cavity and continued in a second nasal cavity. When treatment is initiated in the second nasal cavity, the clock is reset and a new cycle of the treatment procedure starts.

Figure 8C:
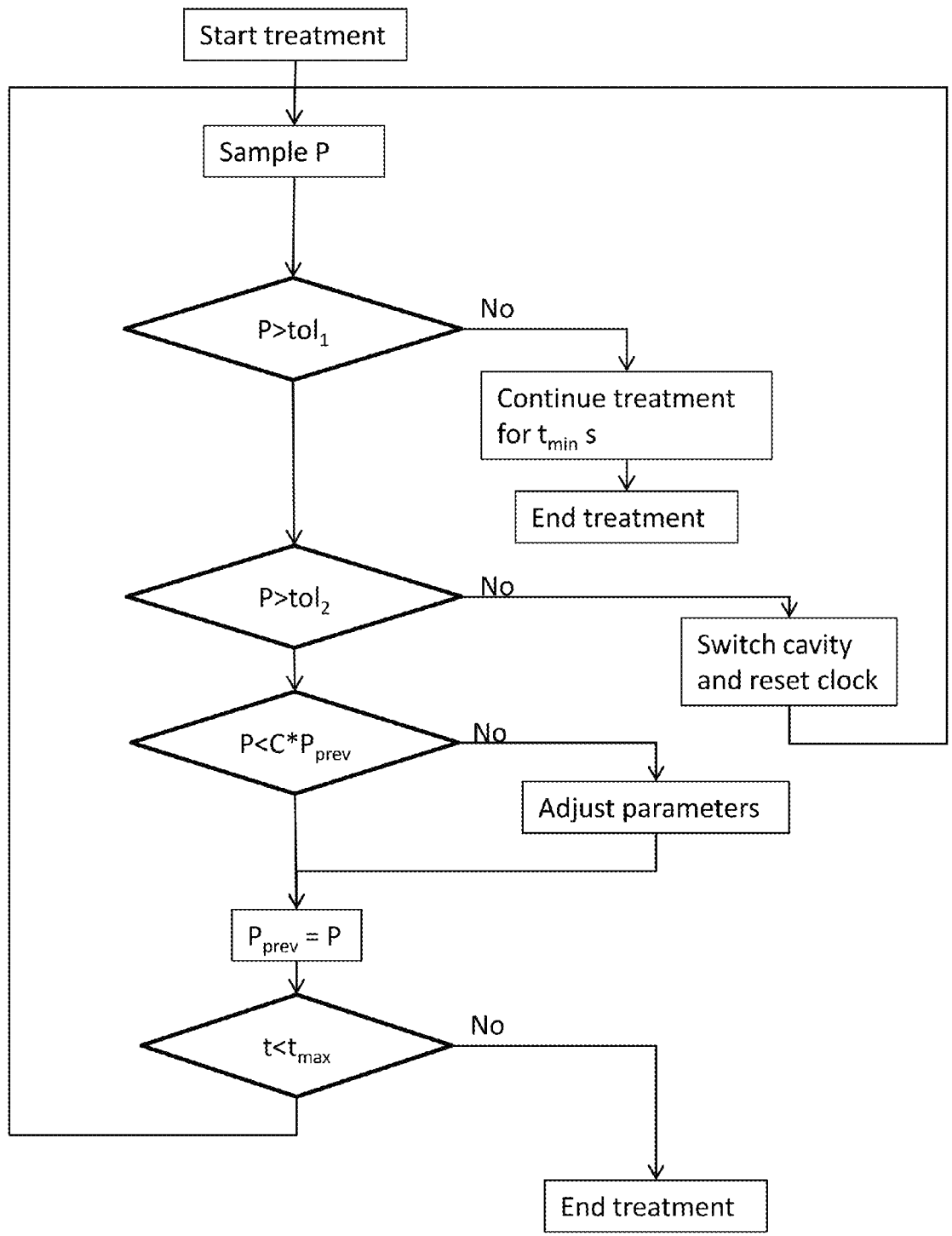

In FIG. 8C, a further example of a treatment procedure is depicted. In similarity with the procedure of FIG. 8A, only a pain measure P is collected during treatment. The pain measures is compared to a first boundary value ($tol_1$). If the pain measure is already smaller than the first boundary value, the treatment should continue for a minimum treatment time ($t_{min}$). Once this time has elapsed, treatment may be ended.

If the pain measure is larger than the first boundary value, then it is compared to a second boundary value ($tol_2$). If the pain measure is not larger than this second boundary value, the treatment may be terminated in a first nasal cavity and continued in a second nasal cavity. When treatment is initiated in the second nasal cavity, the clock is reset and a new cycle of the treatment procedure starts.

If the pain measure however is larger than the second boundary value ($tol_2$), comparison is made with a previous pain measure ($P_{prev}$). If the current pain measure is smaller than the previous pain measure, given appropriate weight in the comparison by the constant C, this means that the pain is being reduced and the treatment is effective. Thus, another cycle of treatment may be initiated provided that a maximum treatment time ($t_{max}$) has not been attained. If the treatment has already been going on for a maximal time period, it should be terminated. Before starting another cycle of the treatment procedure, the current pain measure P is registered as a previous pain measure.

If the current pain measure is larger than the previous pain measure ($C*P_{prev}$), stimulation parameters should be adjusted.

Figure 8D:
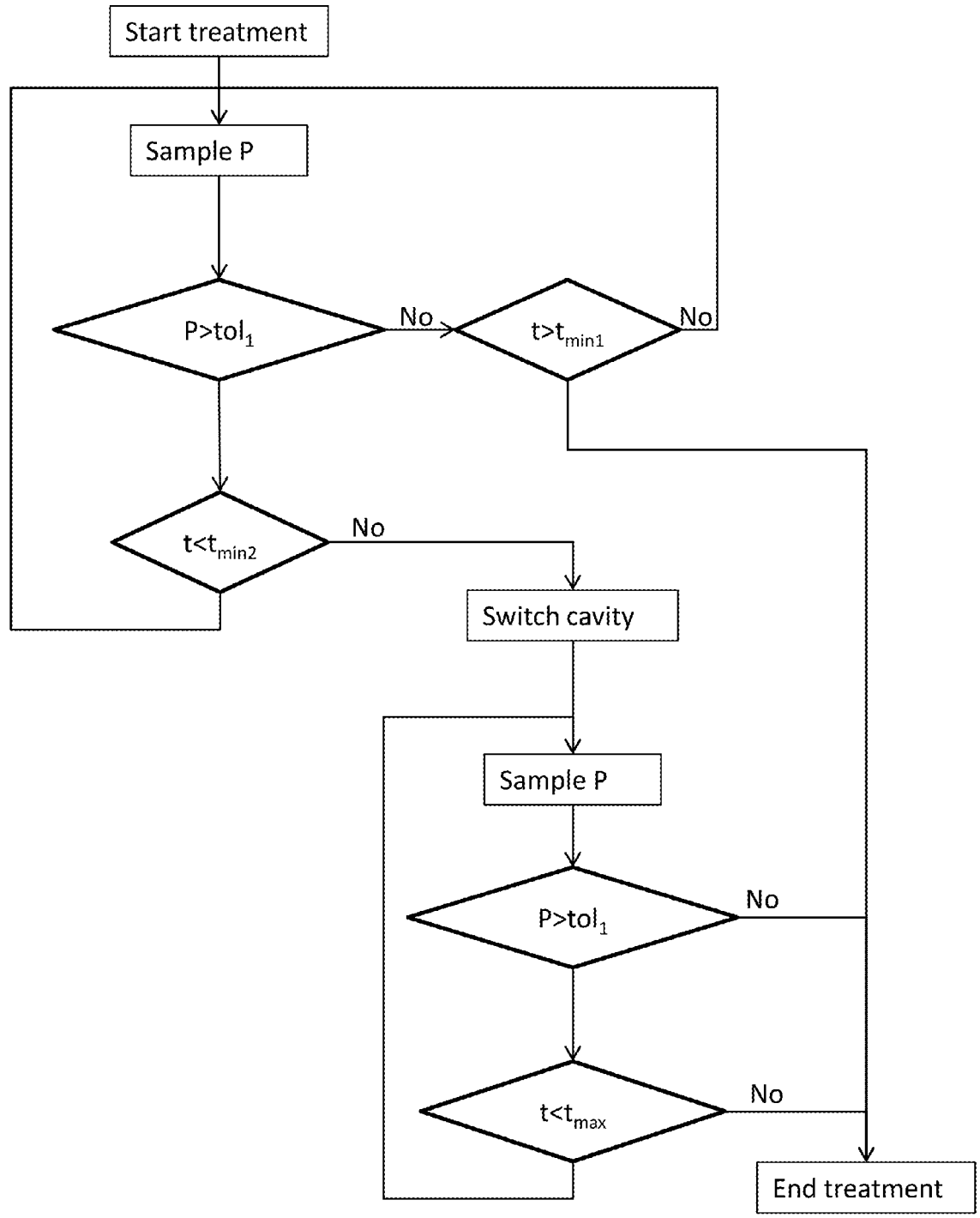

Another example of a treatment procedure is depicted in FIG. 8D. In similarity with the example in FIG. 8A, only a pain measure (P) is collected when initiating a treatment cycle. The pain measure P is compared to a first boundary value ($tol_1$) in similarity with the procedure of FIG. 8A. If the pain measure P has been decreased to an acceptable level such that it does not surpass a first boundary value ($tol_1$), and the treatment duration surpasses a minimum treatment time ($t_{min1}$), the treatment may be terminated. If the minimum treatment time ($t_{min1}$) has not been reached, treatment is continued and a new pain measure may be collected and analyzed in a further treatment cycle.

If the pain measure P has not decreased to an acceptable level, i.e. it still surpasses a first boundary value ($tol_1$), the treatment may be continued in a second nasal cavity provided that a second minimum treatment time ($t_{min2}$) has been reached otherwise a new pain measure may be collected and analyzed in a further treatment cycle.

If treatment is continued in a second nasal cavity a new pain measure is collected and compared to the first boundary value ($tol_1$). If the pain measure has reached an acceptable level treatment may be terminated. Otherwise the elapsed time is compared to a maximum treatment time ($t_{max}$). If the maximum treatment time has not been surpassed a new pain measure may be collected and analyzed in a further treatment cycle, otherwise the treatment may be terminated.

In the above exemplary procedures, independently of each other, $tol_1$ may for example be 1 (if the pain is measured on a VAS scale), $t_{min1}$ may be approximately 2 minutes, $t_{min}$ may be approximately 10 minutes, $t_{min2}$ may be approximately 10 to 15 minutes, $t_{min3}$ may be approximately 15 to 20 minutes and $t_{max}$ may be approximately 30 to 40 minutes.

Clinical Results

Materials and Methods

Pilot tests were conducted with a device and a method according to the invention. The tests were conducted in the nasal cavity of patients with headache disorders.

The stimulation member was a balloon which in an expanded, second state had a diameter of approximately 1.5 cm and a length of 5 cm. The balloon was connected with a tubing having a length of approximately 15 cm. The tubing and the balloon were connected to each other such that one end of the tubing resided within the balloon, having a length of maximally 4 cm to simplify introduction into the nasal cavity. The tubing supplied air to the balloon for expanding the same. The other end of the tubing was connected via a three-way cock to a graduated syringe (20 ml) as well as to another tubing, which was connected to a closed air system. The closed air system was connected to a flexible membrane, which was oscillated with a variable frequency in the interval 10-100 Hz by means of a motor. The air pressure could be varied in a controlled manner within a pressure interval of 20-120 mbar. The amplitude of the oscillating membrane could be varied in a controlled manner (in arbitrary but reproducible units). Prior to use, the balloon was provided with a hygienic protective cover, consisting of a finger from a disposable glove. The hygienic protective cover was dipped in a paraffin solution prior to each introduction into a nasal cavity.

The following general method was used for all treatments:

The device in a first state with the balloon and its hygienic protective cover in a non-expanded state was introduced into the nasal cavity. Inside the nasal cavity, the balloon was expanded to a pressure of 20-120 mbar. By arranging and expanding the balloon in the nasal cavity in this way, a contact surface with the tissue of a desired part of the nasal cavity was established.

Vibrations in the range of 40-100 Hz were achieved by varying the volume in the closed system by controlled movements of the flexible membrane by means of the motor.

The air was then evacuated from the balloon such that the balloon was transferred to a non-expanded state. The balloon was withdrawn from the nasal cavity, and the hygienic protective cover was removed.

If stimulation was conducted in the second nasal cavity as well, a new protective cover, dipped in paraffin solution, was placed over the balloon prior to introduction into the second nasal cavity. Stimulation was performed in the second nasal cavity according to the method above.

The results for the various groups of patients and individuals are described below.

Vibration Treatment of One Patient Suffering from Migraine

Treatment was performed while registering blood oxygen level dependent functional magnetic resonance images (fMRI). The patient estimated the pain before, during and after stimulation on a visual analogue scale (VAS) from 0-10, wherein 0 corresponds to no pain, and 10 corresponds to maximal pain.

Before treatment, the patient had vomited and was experiencing photophobia and nausea. The patient reported a pain level of 10 on the VAS scale. The pain was located to the right part of the head.

The patient was treated while in a horizontal position. The vibratory treatment was started in the right nasal cavity at a pressure of 85-100 mbar. The frequency was set to 68 Hz. After 10 minutes of treatment, the pain level was down to 6 and the nausea was gone. At that point the balloon was moved to the left nasal cavity and treatment continued for another 8 minutes. At this point the patient reported a pain level of 2. After a five minute break the treatment was started again in the right nasal cavity. After about 8 minutes the pain level was down to 1 and the treatment was terminated.

Six months after the treatment the patient reported that no migraine attacks had occurred. Consequently, the effect of the stimulation was long-lasting.

Analysis of the fMRI data showed that the oxygen consumption in the hypothalamus initially was abnormally high whereas during the treatment the consumption decreased to levels similar to the surrounding brain tissue.

Vibration Treatment of a Second Patient Suffering from Migraine

Prior to treatment the patient was suffering from a migraine attack with reported pain level of 8 on a VAS scale. The pain was located to the right side of the head.

Vibration treatment was administered to the right nasal cavity. The frequency used was 68 Hz. The pressure was initially set to between 80 and 100 mbar. After 200 seconds the pressure was lowered to 42 mbar. The patient sensed an increase in pain level. The pressure was returned to the range of 80 to 100 mbar after another 50 seconds.

At 350 seconds the patient started to feel very tired. After 450 seconds of treatment a sharp miosis (constriction of the pupil) was observed. After 600 seconds of treatment the pressure was lowered again to about 40 mbar. After 700 seconds the patient reported that the pain had been reduced to 4-5 on the VAS scale. The pain further decreased to 3 at 875 seconds and 2-3 at 1000 seconds.

The pressure was raised again after 1050 seconds to about 90 mbar. At 1140 seconds the pain had increased slightly to approximately 3-4 on the VAS scale. At 1200 seconds the pressure was reduced to about 40 mbar again. At 1250 seconds the pain level was estimated to 2 on the VAS scale. At 1375 seconds the pain level was 1-2. After about 1400 seconds of treatment the pressure was lowered even further to about 20 mbar. At 1475 seconds the pain level was 1. After 1500 seconds the vibrations were stopped. At 1515 seconds the pain was gone.

1600 seconds after the start of treatment the vibrations were resumed at 68 Hz, the pressure was still about 20 mbar. After another 700 seconds the treatment was terminated. The patient had no headache afterwards. In addition, a pain in the neck experienced prior to treatment was gone. The fatigue experienced during the treatment was also gone.

CONCLUSION

The patients treated according to the above examples have responded well to a stimulation frequency of 68 Hz.

It is not evident what bodily function a particular frequency corresponds to. One possibility would be that any particular frequency or higher harmonics of it correspond to an intrinsic frequency of the mechanoreceptors. Another alternative is that parts of the bone structure where the mechanoreceptors are attached have a resonance that is excited by the applied vibrations. Yet another possibility is that vibrations of the hypothalamus itself or some surrounding tissue at this particular frequency has a beneficial effect.

From the first example above one can infer that a relatively higher pressure affects the hypothalamus and gives a long lasting effect. Based on the findings from the second example, together with what is known from literature, one might conclude that with a lower pressure the SPG is affected, and that this gives immediate pain relief.

What is claimed is:

1. A method for treatment of a headache disorder in a human subject, comprising:
    a) selecting at least one treatment area in the nasal cavity of the human subject, said treatment area being selected from a posterior part of the nasal cavity or an anterior part of the nasal cavity;
    b) providing a device comprising a stimulation member arranged for vibration stimulation of the selected treatment area, and at least one expansion member, said stimulation member being arranged to be expanded by the at least one expansion member, the expansion member being arranged at least partly within the stimulation member and provided with a channel having a plurality of openings arranged for fluid communication with the stimulation member, and wherein a bending stiffness of the expansion member in a first direction perpendicular to a longitudinal direction of the expansion member is different from a bending stiffness in a second direction perpendicular to said first direction and to the longitudinal direction of the expansion member;
    c) introducing the stimulation member into a nasal cavity of the human subject;
    d) expanding the stimulation member to a volume such that the stimulation member abuts against the tissue to exert a pressure on tissue of the selected treatment area; and
    e) bringing the stimulation member to vibrate in the nasal cavity to impart vibrations to the selected treatment area,
    wherein the vibrations are imparted:
        to a posterior part of the nasal cavity;
        to an anterior part of the nasal cavity;
        sequentially to a posterior and an anterior part of the nasal cavity; or
        simultaneously to a posterior and an anterior part of the nasal cavity.

2. The method according to claim 1, further comprising the step of imparting vibrations at at least one frequency selected from the range of approximately 40 to 100 Hz.

3. The method according to claim 1, further comprising the step of exerting a pressure of between approximately 20 and 120 mbar on the tissue of the nasal cavity.

4. The method according to claim 3, further comprising the step of initially exerting a first pressure on the tissue and subsequently exerting a second pressure on the tissue.

5. The method according to claim 4, wherein the pressures are selected from a range of between 20 and 80 mbar or from a range of between 81 and 120 mbar, wherein the first and second pressures are not selected from the same range.

6. The method according to claim 1, further comprising the steps of:
    obtaining an input signal reflecting a measure of a level of pain experienced by the human subject; and
    analyzing the input signal and performing one or more acts to decrease the input signal reflecting a measure of pain, wherein the acts are selected from:
        adjusting a frequency of the vibrations imparted to the nasal cavity;
        adjusting an amplitude of the vibrations imparted to the nasal cavity;

adjusting a pressure exerted on the tissue of the nasal cavity; or terminating vibration stimulation in a first nasal cavity and optionally continuing vibration stimulation in a second nasal cavity.

7. The method according to claim 6, further comprising the steps of:
calculating and analyzing a derivative of the input signal reflecting a measure of pain; and
performing one or more of said acts.

8. The method according to claim 6, wherein one or more of the acts are performed when either the input signal reflecting a measure of pain pass a first threshold, or when a derivative of the input signal passes a second threshold.

9. The method according to claim 6, further comprising the step of terminating the treatment in the nasal cavity when either the input signal reflecting a measure of pain falls below a third threshold, when a maximum treatment time has elapsed, or when the derivative of the input signal is zero or within a derivative tolerance.

10. The method according to claim 6, wherein said adjusting further comprises an adjustment selected from:
a random adjustment;
an amount calculated as a function of an elapsed treatment time, an initial value of the input signal reflecting a measure of pain, and a current value of the input signal reflecting a measure of pain; and
an amount calculated as a function of a derivative of the input signal reflecting a measure of pain and a time development of the pressure, frequency, and amplitude during the treatment.

11. The method according to claim 6, wherein the input signal reflecting a measure of pain is obtained by fMRI.

12. The method according to claim 6, wherein the input signal reflecting a measure of pain is an index on a visual analog scale (VAS).

13. The method according to claim 6, wherein the input signal reflecting a measure of pain is provided by the human subject.

14. The method according to claim 6, wherein the human subject suffers from a headache disorder selected from cluster headache, migraine, tension-type headache and medication-overuse headache.

15. The method according to claim 1, further comprising the step of adjusting at least one of a pressure, a frequency and an amplitude of the vibrations, and repeating steps a) d) and e).

16. The method according to claim 1, further comprising the steps of:
bringing the stimulation member to an essentially non-expanded state; removing the stimulation member from the nasal cavity; and
repeating steps a) to e) in a second nasal cavity of the human subject.

17. The method according to claim 1, wherein the treatment target is selected from hypothalamus and sphenopalatine ganglion.

18. The method according to claim 1, wherein the stimulation member comprises at least one retaining portion and at least one stimulating portion.

19. The method according to claim 1, wherein said providing comprises displaying information in a user interface on a type of stimulation member to use for the selected treatment area.

20. The method according to claim 19, wherein the user interface is arranged to display the time evolution of an input signal during the treatment duration.

21. The method according to claim 1, the method further comprising providing at least one of:
a frequency regulating module arranged to control the frequency of the vibrations imparted by the stimulating member to the nasal cavity and
an amplitude regulating module arranged to control the amplitude of the vibrations imparted by the stimulating member, and a pressure regulating module arranged to control the pressure at which the stimulating member abuts against the tissue.

22. The method according to claim 21, further comprising providing a control unit arranged to direct vibrations to at least one of the posterior and the anterior part of the nasal cavity by controlling operation of said regulating modules.

23. The method according to claim 1, wherein the stimulation member further comprises at least one of an anterior stimulating portion arranged to abut against tissue of the anterior part of the nasal cavity and to impart vibrations to the anterior part of the nasal cavity, and a posterior stimulating portion arranged to abut against tissue of the posterior part of the nasal cavity and to impart vibrations to the posterior part of the nasal cavity.

\* \* \* \* \*